(12) United States Patent
Kusuzawa et al.

(10) Patent No.: US 6,707,555 B1
(45) Date of Patent: Mar. 16, 2004

(54) OPTICAL INFORMATION MEASURING APPARATUS

(75) Inventors: Hideo Kusuzawa, Kobe (JP); Yasuyuki Imura, Kobe (JP); Hironori Kobayashi, Kobe (JP); Masaki Ishisaka, Himeji (JP)

(73) Assignee: SYSMEX Corporation, Hyogo (JP)

( * ) Notice: Subject to any disclaimer, the term of this patent is extended or adjusted under 35 U.S.C. 154(b) by 0 days.

(21) Appl. No.: 09/411,656

(22) Filed: Oct. 4, 1999

(30) Foreign Application Priority Data

Oct. 15, 1998  (JP) ............................. 10-294041

(51) Int. Cl.⁷ ............................................. G01N 21/00
(52) U.S. Cl. ....................................... 356/436; 356/440
(58) Field of Search ............................... 356/436, 440; 359/821, 823, 822, 696

(56) References Cited

U.S. PATENT DOCUMENTS

| | | | | |
|---|---|---|---|---|
| 3,580,681 A | * | 5/1971 | Robert et al. | 356/437 |
| 3,758,217 A | * | 9/1973 | Stokstad | 359/821 |
| 4,787,750 A | * | 11/1988 | Nelson et al. | 356/437 |
| 5,828,502 A | * | 10/1998 | Afshari | 359/822 |
| 5,943,122 A | | 8/1999 | Holmes | |
| 6,122,114 A | * | 9/2000 | Sudo et al. | 359/822 |

FOREIGN PATENT DOCUMENTS

| | | |
|---|---|---|
| EP | 0841555 | 5/1998 |
| GB | 2133901 | 8/1984 |
| JP | A6160723 | 6/1994 |
| WO | WO9745718 | 12/1997 |
| WO | WO9960380 | 11/1999 |

* cited by examiner

*Primary Examiner*—Frank G. Font
*Assistant Examiner*—Amanda Merlino
(74) *Attorney, Agent, or Firm*—Birch, Stewart, Kolasch & Birch, LLP

(57) ABSTRACT

An optical information measuring apparatus includes: a light source section capable of emitting a plurality of light beams; a light guiding section for directing and supplying the plurality of light beams from the light source section to an object; an object lens arranged facing the object; a plurality of light receiving sections for respectively receiving the light beams from the object via the object lens; and a frame section for integrally mounting a plurality of optical elements including the light source section, the light guiding section, the object lens, and the light-receiving sections.

26 Claims, 23 Drawing Sheets

OPTICAL INFORMATION MEASURING APPARATUS

CROSS-REFERENCES TO RELATED APPLICATIONS

This application is related to Japanese patent applications No. HEI 10-294041 filed on Oct. 15, 1998 whose priority is claimed under 35 USC §119, the disclosure of which is incorporated herein by reference in its entirety.

BACKGROUND OF THE INVENTION

1. Field of the Invention

The present invention relates to an optical information measuring apparatus, and more particularly to an apparatus suitably usable, for example, as a particle analyzing apparatus (imaging flow cytometer) having an image capturing function.

2. Description of the Related Art

A conventional particle analyzing apparatus having an image capturing function includes optical elements for particle detection and image capturing. These optical elements are disposed on a two-dimensional optical fixed board, and their positions are determined in optical alignment. In other words, the position, the directions of optical axes, the height, the parallel degree, and the like of these optical elements with respect to the fixed board are adjusted to ensure accurate alignment of each other.

However, in such a conventional apparatus, a large number of optical elements disposed dispersedly on the two-dimensional optical fixed board increase the size of the apparatus as a whole and provide poor transportability. Also, it is not easy to align the optical elements. The present invention has been made in view of these circumstances, and provides an optical information measuring apparatus with compact size and good transportability. Also, the present invention facilitates alignment of the optical elements with a higher precision.

SUMMARY OF THE INVENTION

The present invention provides an optical information measuring apparatus comprising: a light source section capable of emitting a plurality of light beams; a light guiding section for directing and supplying the plurality of light beams from the light source section to an object; an object lens; a plurality of light receiving sections for respectively receiving the light beams from the object via the object lens; and a frame section for integrally mounting a plurality of optical elements including the light source section, the light guiding section, the object lens, and the light-receiving section. The word "integrally" as used herein means that the plurality of optical elements are optically aligned and integrated into a single structural member for transportability.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Figure 1:
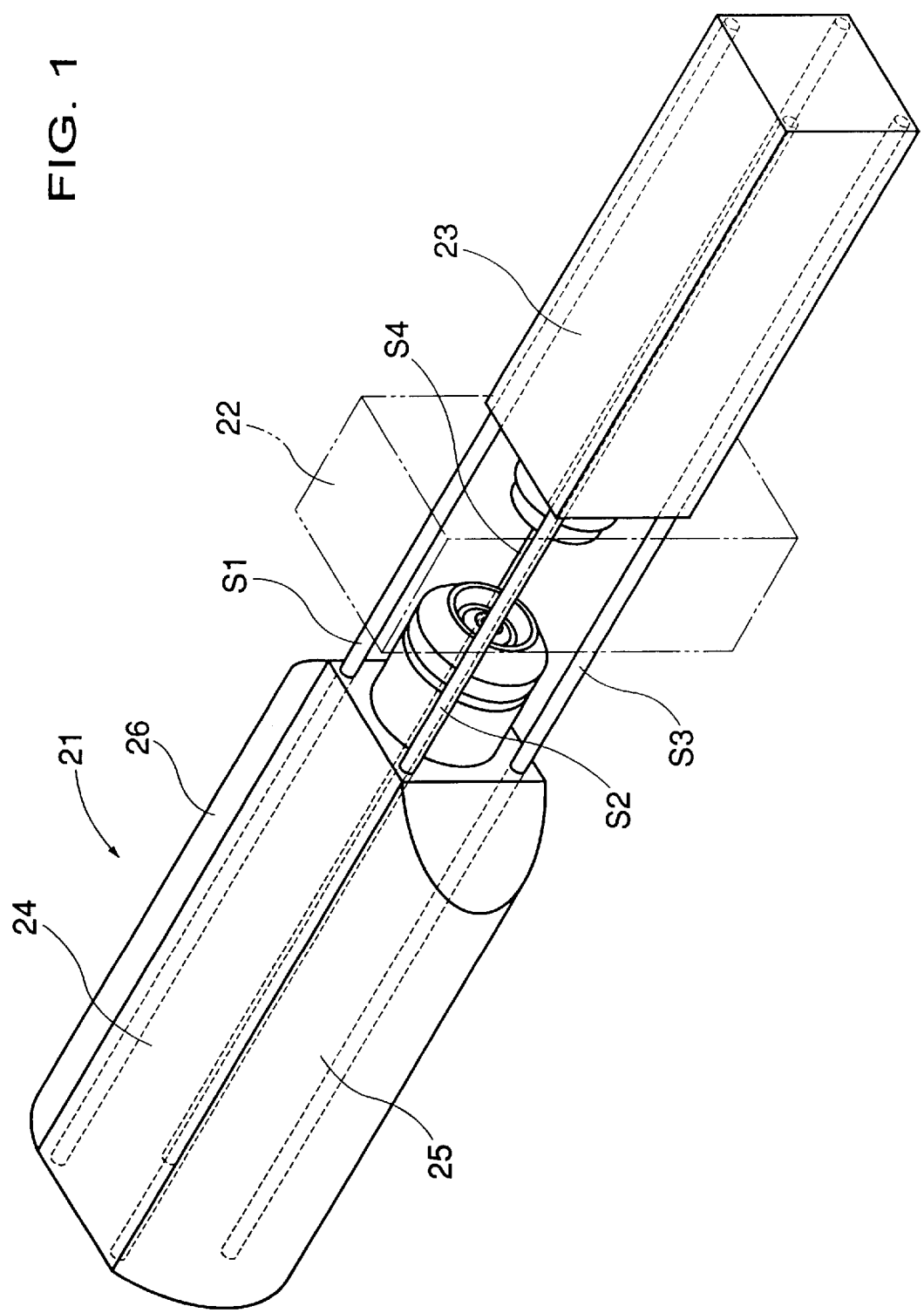
FIG. 1 is a perspective view showing an overall construction of an apparatus according to an embodiment of the present invention.

The light source section of the present invention may include a plurality of light sources each emitting a light beam of a different wavelength. The light source may be, for example, a laser diode, a pulse laser diode, a LEF), or the like.

The light source section may include a first light source emitting a light beam of a first wavelength and a second light source emitting a light beam of a second wavelength, and the light receiving section may include a first light receiving element for receiving the light beam of the first wavelength from the object and a second light receiving element for receiving the light beam of the second wavelength from the object. In this case, the first light source may be a continuous emission laser light source such as a laser diode, and the second light source may be a pulse emission laser light source such as a pulse laser diode.

Further, the first light receiving element may be a light receiving element for detecting an intensity of the light beam, and the second light receiving element may be an image capturing element for capturing an image of the object. Two kinds of optical information may be obtained from the object by means of the first and second light receiving elements.

In the present invention, optical information obtained from the plurality of light receiving sections is processed and converted into measurement data by a information processing device such as a personal computer.

The light beams to be supplied from the light source section to the object may differ in wavelength or radiating form. The light beams to be supplied to the object may include a plurality of light fluxes having an annular cross section which are coaxial with an optical axis of the object lens. Use of such a type of radiation may reduce unnecessary light beams such as background light as compared with other types of radiation, thereby enabling clear detection or capturing an image of a smaller object.

To be more specifically described, the light source section may be constructed with a light guiding element having an inlet section and an outlet section of the light beams, a plurality of light sources disposed around an optical axis of the light guiding element, a light condensing element for guiding the light beams from the plurality of light sources to the inlet section, and a converting element for converting the light beams from the outlet section into a light flux having an annular cross section.

The light sources may be laser light sources, and the light guiding element may be a coherence reducing element, such as an optical fiber, for reducing a coherence of a laser light beam.

The light beam to be supplied from the light source section to the object may pass through an optical path having a center at the optical axis of the object lens.

The light source section may include, for example, first, second, and third light sources for respectively emitting light beams of first, second, and third wavelengths; the light guiding section may include an optical element for converting the laser beams of the first and second wavelengths into light fluxes having an annular cross section and for guiding the light fluxes to the object from an outside of the object lens, and an optical element for guiding the light beam of the third wavelength to the object via the object lens; and the light receiving section may include a first light receiving element for receiving the light beam of the first wavelength from the object, and second and third light receiving elements for respectively receiving the light beams of the second and third wavelengths from the object. In this case, a further more optical information may be obtained from the object. The third light receiving element may be an image capturing element for capturing an image of the object.

The light guiding section of the present invention includes a lens, a plane mirror, a ring-shaped plane mirror, a ring-shaped concave mirror, a conical mirror, a dichroic mirror, or a combination of these.

The light guiding section may include an element for guiding the light beam from the light source section to the object from an outside of the object lens. The light guiding section may include an element for guiding the light beam from the light source section to the object via the object lens. The light guiding element may include an element for converting the light beam from the light source section into a light flux having an annular cross section and for guiding the light flux to the object from an outside of the object lens.

The light receiving section includes an image capturing element such as a CCD, and an optical detecting element such as a photodiode or a photomultiplier tube.

The light receiving section may include an optical detecting element for detecting an intensity of the light beam from the object and an image capturing element for capturing an image of the object.

The frame section more preferably includes a plurality of block members for mounting the plurality of optical elements and a connecting member for connecting the block members so that the block members are arranged with a spacing.

In view of facilitating the positioning with more precision, the frame section more preferably includes a plurality of block members and a shaft member for passing through the block members to fix the block members so that the block members are arranged with a predetermined spacing.

The frame section may include an outer peripheral surface and a hollow section; the light source section may be mounted on the outer peripheral surface; and the light guiding section, the object lens, and the light receiving section may be mounted in the hollow section.

The frame section may include an outer peripheral surface and an elongate hollow section; the light source and the light receiving section may be mounted on the outer peripheral surface; and the light guiding section and the object lens may be mounted in the hollow section.

The frame section may include a plurality of block members and a connecting member for connecting the block members; and the optical elements such as the light source section, the light guiding section, the object lens, and the light receiving section may be mounted on the respective corresponding block members.

The optical information measuring apparatus of the present invention may further include an auxiliary frame section connected to the frame section and a placing section for placing the object, wherein the placing section may be mounted on the auxiliary frame section.

The optical information measuring apparatus of the present invention may further include a second light source section for supplying a light beam to the object, and the second light source section may be mounted on the auxiliary frame section and positioned to face the object lens with the placing section disposed therebetween.

The auxiliary frame section may be constructed commonly with a plurality of shaft members to be used for passing through the block members of the frame section to fix the block members.

The block member to be used in the frame section may be, for example, a square or rectangular flat plate. However, the block member may be a circular plate, an L-shaped plate, or a plate having a shape of "⊐". The block member is not limited to a flat plate alone, and may have a more complex shape. If a metal is to be used as a material of the block member, the block member is preferably made of aluminum in view of reducing the weight. Also, a hard resin (for example, ABS) may be used as a material of the block member. The shaft member may be made, for example, of a commercially available cylindrical rod made of stainless steel.

Each block member has through-bores for passing a plurality of shaft members in a parallel direction therethrough. These through-bores for the shaft members may be formed by simultaneously drilling a plurality of superposed block members. By this simultaneous drilling of the block members, the precision of the position of the through-bores is improved. In view of ensuring the strength of the frame section, it is preferable to provide three or more shaft members.

Each block member may be fixed to the shaft member, for example, by using a screw for pressing the shaft member from a side surface of the block member, or by fixing to the shaft member a member that holds the block member on the shaft member from both sides of the block member.

It is preferable that one of the block members has an opening section and the object lens is mounted in the opening section so that the optical axis of the object lens is parallel to the shaft members. This makes it easier to direct or position the optical axis in mounting the light source section or the light receiving section to the block member.

At least one of the block members may have a side surface parallel to the shaft members, and the light source section may be mounted on the side surface. The light receiving section may be mounted on another of the block members.

At least one of the block members may have a side surface parallel to the shaft members and the light receiving section may be mounted on the side surface.

The apparatus of the present invention may further include a mirror that guides a light beam from the object lens to the light receiving section, and the mirror may be mounted on one of the block members.

The apparatus of the present invention may further include a mirror that guides a light beam from the light source section to the object lens, and the mirror may be mounted on one of the block members.

The apparatus of the present invention may further include a ring-shaped mirror mounted on one of the block members; the light source section may include a light source for radiating a light flux having an annular cross section; and the ring-shaped mirror may guide the light flux having an annular cross section from the light source section to an outer circumference of the object lens.

The apparatus of the present invention may further include an imaging lens disposed on an optical path between the object lens and the light receiving section, and the imaging lens may be mounted on one of the block members.

The apparatus of the present invention may further include a placing section for placing the object and an auxiliary shaft member detachably attached to the frame section in parallel with the shaft members, and the placing section may be connected to the frame section by means of the auxiliary shaft member.

The apparatus of the present invention may further include a second light source section, and the second light source section may be connected to the placing section by means of the auxiliary shaft member so that the light beam of the second light source section is transmitted through the object to be received by the light receiving section via the object lens.

The block members may include central through-bores formed in parallel with the shaft members; the object lens may be mounted on one of the central through-bores; and the light source section, the light guiding section, and the light receiving section may be mounted on the frame section so that an optical path from the light source to the object and an optical path from the object to the light receiving section pass through at least one of the central through-bores.

EXAMPLES

Hereafter, the present invention will be described in detail based on the embodiments shown in the attached drawings, which are not intended to limit the scope of the present invention.

FIG. 1 is a perspective view showing an overall construction of an optical information measuring apparatus according to the present invention. A main body 21 includes a first unit (frame section) 24, a second unit (light source section) 25, and a third unit (light receiving section) 26. Further, a fourth unit (placing section) 22 for placing an object and a fifth unit (second light source section) 23 are detachably connected to the main body 21 by means of four auxiliary shafts S1 to S4 (having a circular cross section with a diameter of 6 mm). The auxiliary shafts S1 to S4 constitute the auxiliary frame section.

Construction of a First Unit (Frame Section) 24

Figure 2:
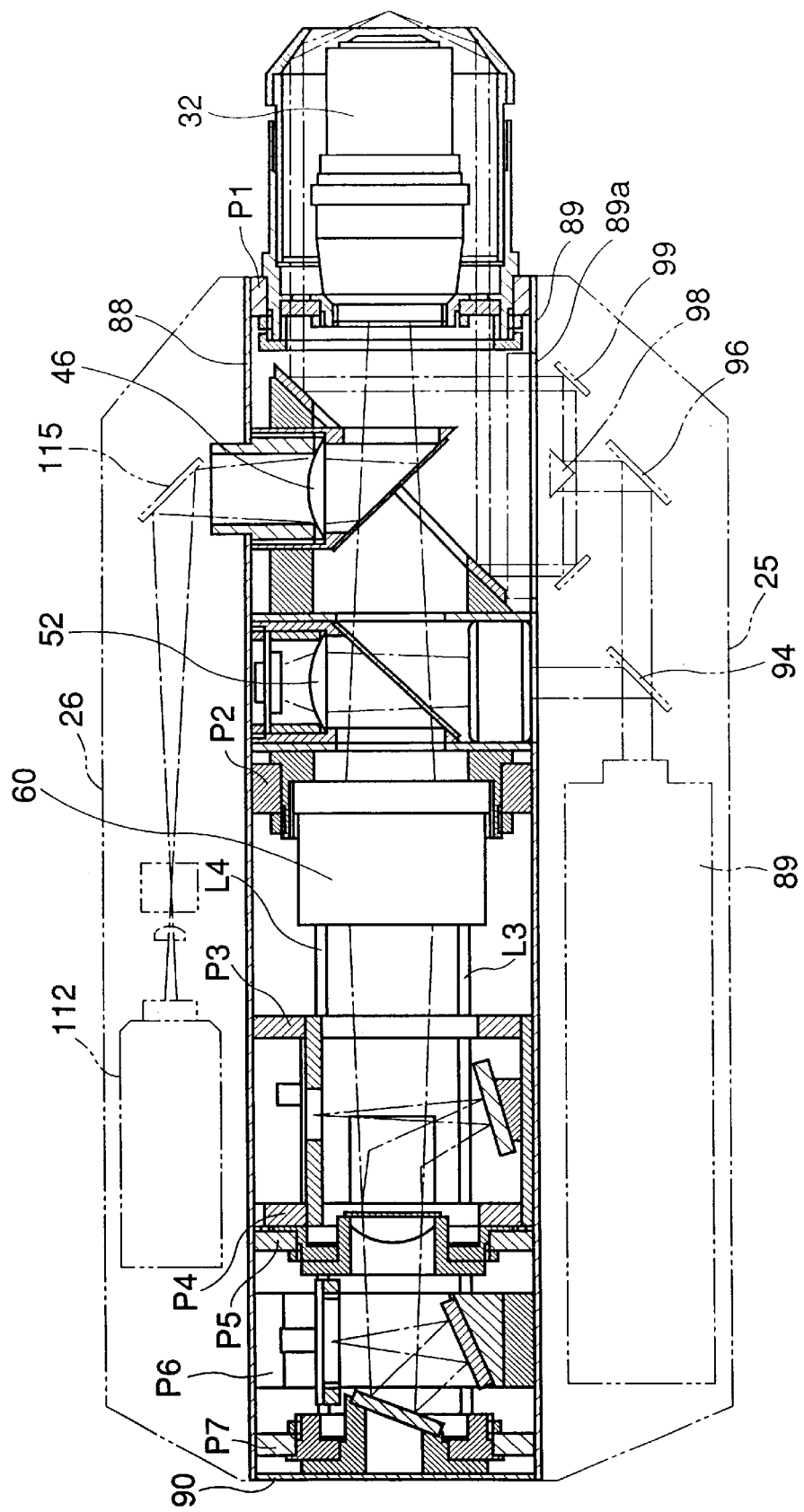
FIG. 2 is a cross-sectional view showing a frame section of the apparatus according to the embodiment of the present invention.
Figure 3:
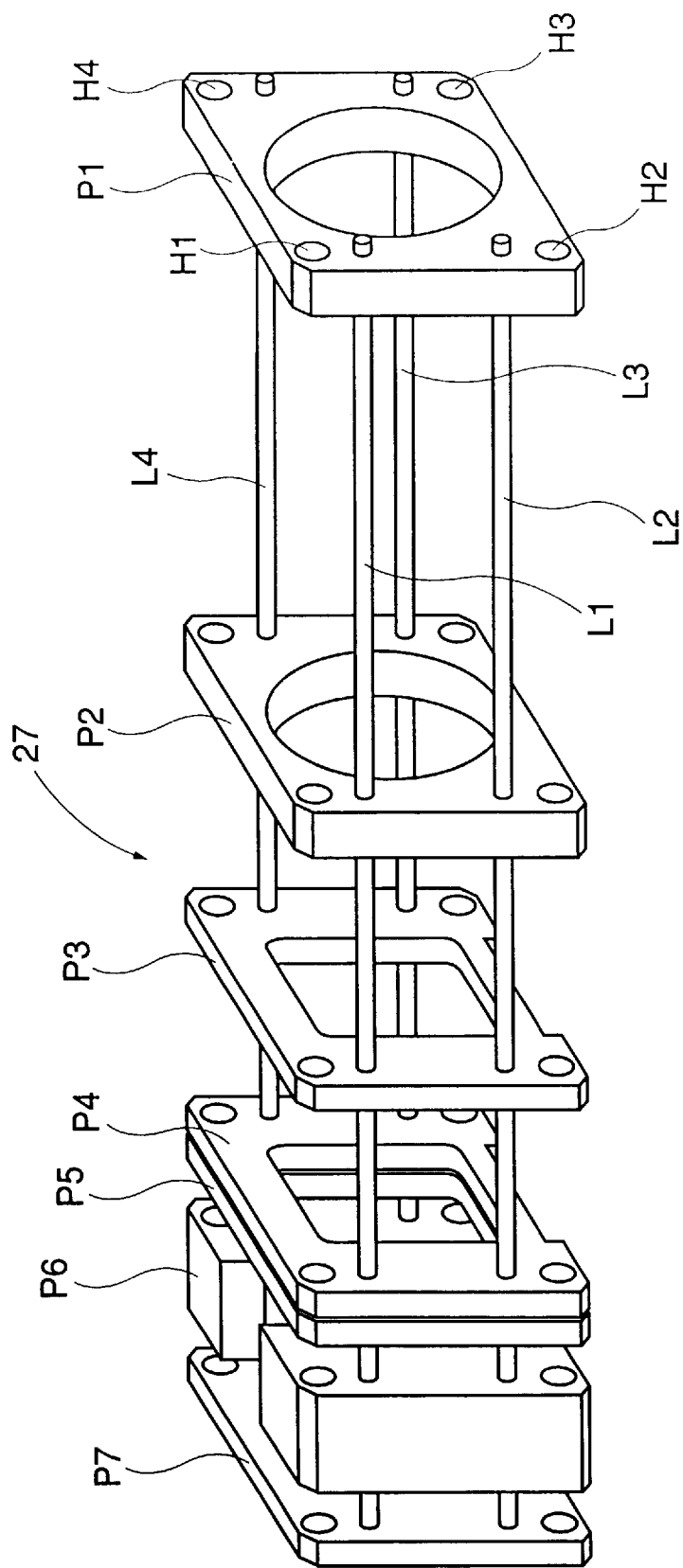
FIG. 3 is a perspective view showing a frame to be used in the frame section according to the embodiment of the present invention.

FIG. 2 is a cross-sectional view of the frame section 24, and FIG. 3 is a perspective view of a frame 27 included in the frame section 24. As shown in these figures, the frame 27 includes seven rectangular plate-shaped block members (hereafter referred to as plates) P1 to P7 (58 mm×54 mm) and four connecting members (hereafter referred to as main shafts) L1 to L4 (having a circular cross section with a diameter of 3 mm). The main shafts L1 to L4 pass through the plates P1 to P7 substantially vertically, whereby the seven plates P1 to P7 are arranged in parallel to each other with a predetermined spacing and fixed to the shafts L1 to L4. Here, necessary optical elements are mounted on the plates P1 to P7 in the following manner before the plates P1 to P7 are fixed by the main shafts L1 to L4.

Figure 4:
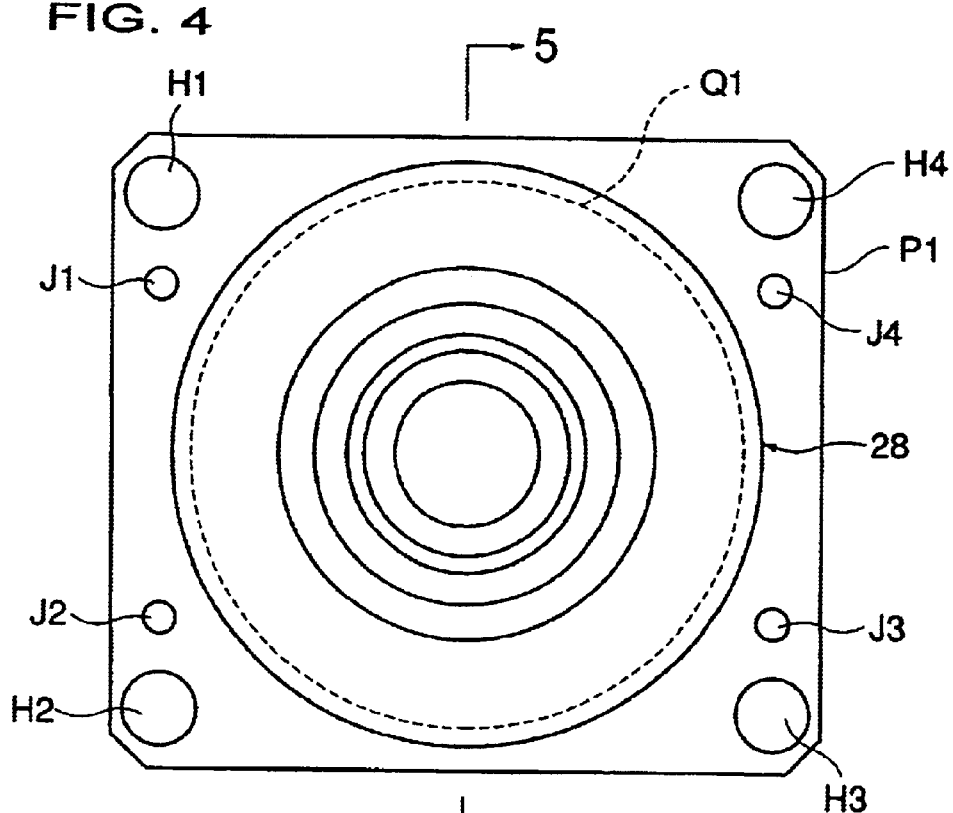
FIG. 4 is a front view showing a first optical element section according to the embodiment of the present invention.

First, the plate P1 is a rectangular flat plate such as shown in FIG. 4, and includes a circular opening Q1 at a central portion thereof. Around the opening Q1 are disposed holes H1 to H4 for inserting auxiliary shafts S1 to S4 (FIG. 1), respectively, and holes J1 to J4 for passing the main shafts L1 to L4 (FIG. 3) therethrough. A first optical element section 28 is fixed to the opening Q1.

Figure 5:
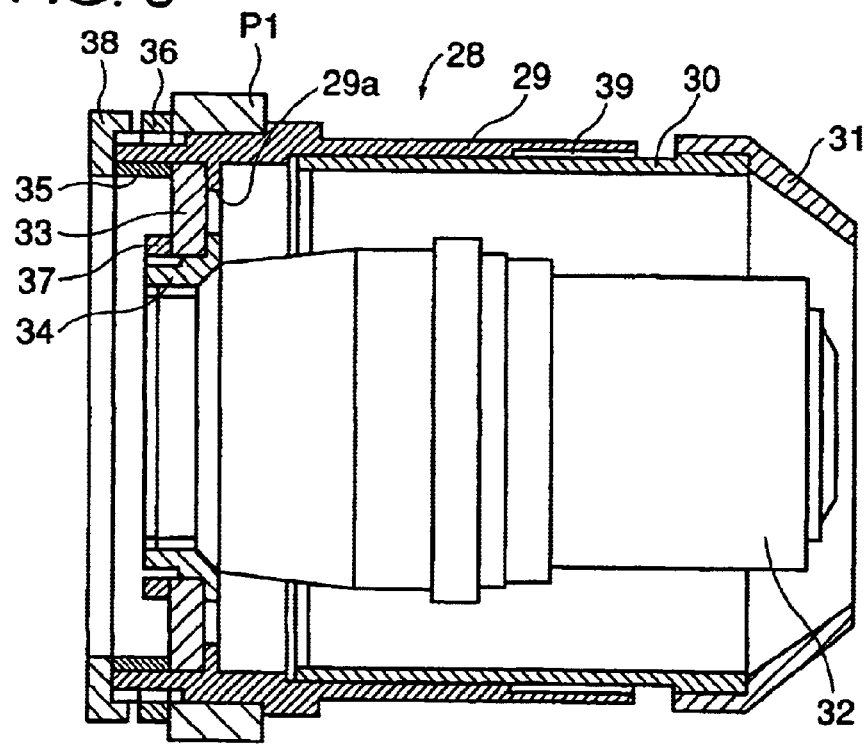
FIG. 5 is a cross-sectional view cut along the line A—A of FIG. 4.

Referring to FIG. 5, the first optical element section 28 includes an outer tube 29, an inner tube 30, an internal-reflection conical mirror 31, an object lens 32, a light-transmitting ring 33, a collar 34 for fixing the object lens, a press ring 35, and nuts 36 to 38.

The internal-reflection conical mirror 31 is attached to a front end of the inner tube 30. The inner tube 30 is inserted into the outer tube 29 from its front end and an outer thread formed on the inner tube 30 engages with an inner thread formed at a front end of the outer tube 29. A rear end of the outer tube 29 is inserted into the opening Q1 of the plate P1, and the outer tube 29 is fixed to the plate P1 by engaging and screwing the nut 36 onto an outer thread formed on an outer circumference at a rear end of the outer tube 29.

In the meantime, after an outer thread at the rear end of the object lens 32 is engaged with an inner thread formed on an inner circumferential surface of the collar 34, the light-transmitting ring 33 is inserted onto the outer circumference of the collar 34, and the light-transmitting ring 33 is fixed to the collar 34 by engaging and screwing the nut 37 with an outer thread of the collar 34.

The object lens 32 is inserted from a rear end of the outer tube 29, and the press ring 35 is inserted into the rear end of the outer tube 29 with the light-transmitting ring 33 abutting against a projection 29a that projects into an inner surface of the outer tube 29, and the light-transmitting ring 33 is fixed to the projection 29a by engaging and screwing the nut 38 onto an outer thread at the rear end of the outer tube 29. Thus, the first optical element section 28 including the object lens 32, the light-transmitting ring 33, and the internal-reflection conical mirror 31 is fixed to the plate P1 so as to be coaxial with the opening Q1.

Figure 6:
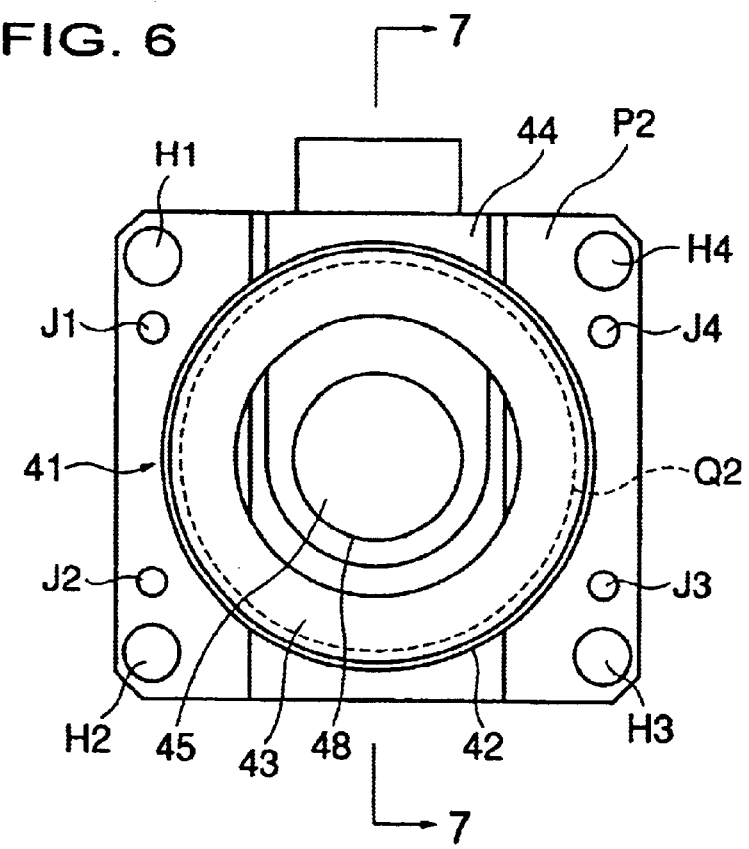
FIG. 6 is a front view showing a second optical element section according to the embodiment of the present invention.

Next, the plate P2 is a rectangular flat plate as shown in FIG. 6, and includes a circular opening Q2 at a central portion thereof. Around the opening Q2 are disposed holes H1 to H4 for inserting auxiliary shafts S1 to S4 (FIG. 1) and holes J1 to J4 for passing the main shafts L1 to L4 (FIG. 3) therethrough. A second optical element section 41 shown in FIG. 7 is assembled in the following manner and fixed to the opening Q2.

First, a ring-shaped mirror 43 is attached to a front end of a tubular member 42 having a cut-out portion formed at a front end at an angle of 45° relative to the axis center. Next, with respect to a tubular member 44 having a cut-out portion formed at a front end at an angle of 45° relative to the axis center, a dichroic mirror 45 is attached to the cut-out portion. A condensing lens 46 is inserted into the inside of the tubular member 44, and the tubular member 47 having an outer thread is engaged and screwed onto the inner thread of the tubular member 44 to fix the lens 46.

Figure 7:
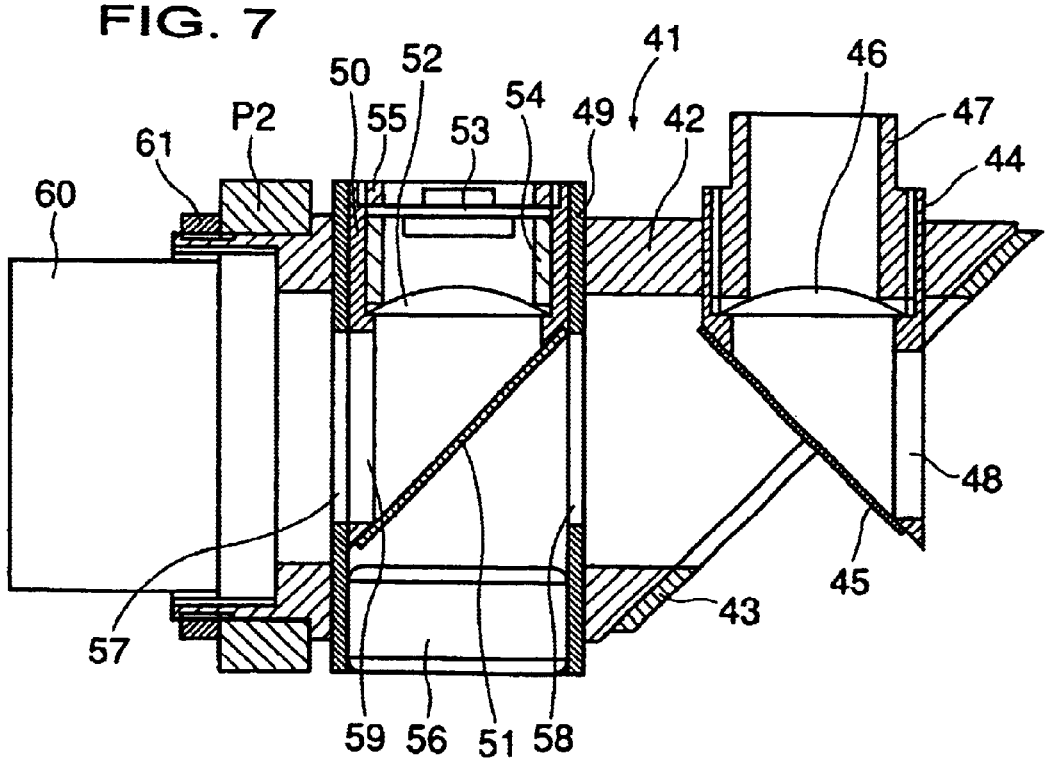
FIG. 7 is a cross-sectional view cut along the line B—B of FIG. 6.

The tubular member 44 is inserted into a through-hole formed perpendicularly in advance in the tubular member 42 and attached to it at a position shown in FIG. 7. At this time, the axis centers of the tubular member 42 and the tubular member 44 intersect with each other perpendicularly. The tubular member 44 includes a circular opening 48, and the center of the opening 48 coincides with the axis center of the tubular member 42.

The tubular member 49 is inserted into a through-hole formed perpendicularly in advance in the tubular member 42. The tubular member 49 passes through the tubular member 42 so that the axis center of the tubular member 49 intersects with the axis center of the tubular member 42. A tubular member 50 is inserted into the tubular member 49, and a half mirror 51 is attached to a cut-out portion formed at an angle of 45° at a front end of the tubular member 50.

Further, a lens 52 and a CCD board camera 53 serving as an image capturing element are fixed to the inside of the tubular member 50 by means of a ring 54 and a washer 55 with an external thread. A beam expander 56 is placed at a lower end of the tubular member 49. The tubular members 49 and 50 have circular openings 57, 58, 59 which are coaxial with the axis center of the tubular member 42.

After the external thread formed on an outer circumference at an end of the object lens 60 is engaged with the inner thread formed on an inner circumference at a rear end of the tubular member 42, the rear end of the tubular member 42 is inserted into the opening Q2 of the plate P2 and fixed onto the plate P2 by means of the nut 61. At this time, the tubular member 42, the object lens 60, and the opening Q2 are coaxial with each other.

Here, the dichroic mirror 45 of the second optical element section 41 to be used in the present invention reflects a light beam having a wavelength of 635 nm, and transmits light beams having wavelengths of 780 nm and 880 nm. The CCD board camera 53 to be used in the present invention has a size of ¼ inch.

Figure 8:
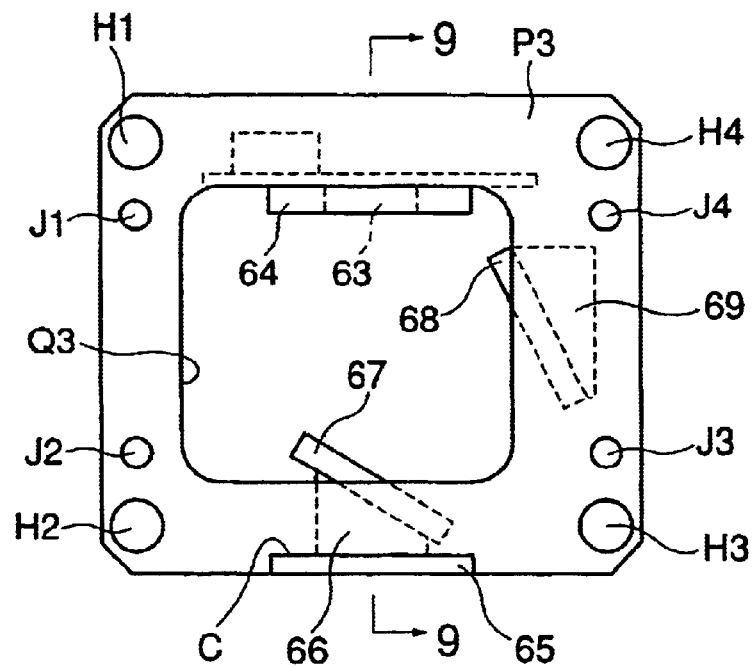
FIG. 8 is a front view showing a third optical element section according to the embodiment of the present invention.
Figure 9:
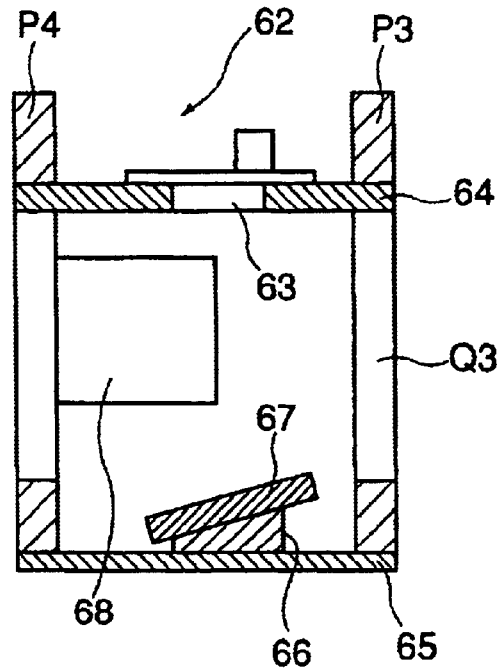
FIG. 9 is a cross-sectional view cut along the line C—C of FIG. 8.

Next, a third optical element section 62 is mounted onto the plates P3 and P4, as shown in FIGS. 8 and 9. The plate P3 is a rectangular flat plate such as shown in FIG. 8, and includes a square opening Q3 at a central portion thereof. Around the opening Q3 are disposed holes H1 to H4 for inserting the auxiliary shafts S1 to S4 (FIG. 1) and holes J1 to J4 for passing the main shafts L1 to L4 (FIG. 3) therethrough. The pilate P3 includes a cut-out portion C at its lower side. The plate P4 also has a shape similar to the plate P3, and includes an opening, holes, and a cut-out portion similar to those of the plate P3.

A ½-inch-size CCD board camera 63 serving as an image capturing element is mounted on a holding plate 64, and the holding plate 64 is fixed to an upper inner wall surfaces of the openings Q3, Q4 of the plates P3, P4 by screws (not shown). The holding plate 65 is mounted onto the cut-out portions C of the plates P3, P4, and fixed to the lower side surfaces of the plates P3, P4 by screws (not shown).

A holding piece 66 is fixed on an upper surface of the holding plate 65, and a plane mirror 67 is attached onto the holding piece 66. A holding piece 69 that holds the plane mirror 68 is fixed onto a surface of the plate P4 facing the plate P3 by a screw (not shown).

Figure 10:
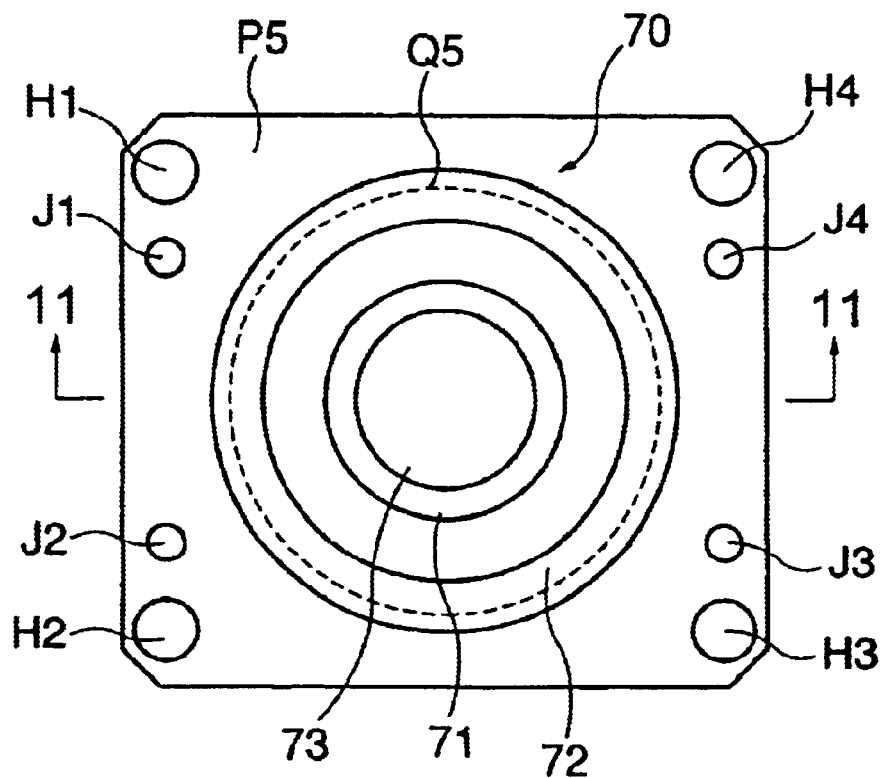
FIG. 10 is a front view showing a fourth optical element section according to the embodiment of the present invention.
Figure 11:
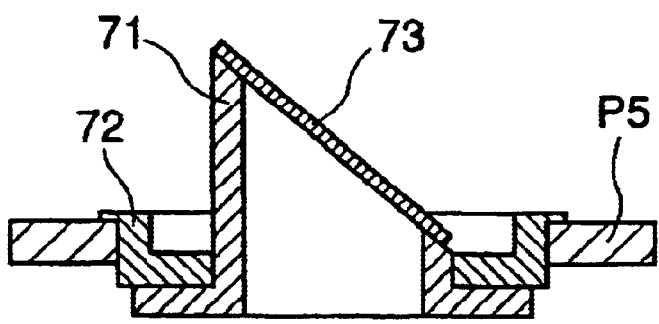
FIG. 11 is a cross-sectional view cut along the line D—D of FIG. 10.

Next, a fourth optical element section 70 is mounted onto the plate P5 as shown in FIGS. 10 and 11. The plate P5 is a rectangular flat plate such as shown in FIG. 10, and includes a circular opening Q5 at a central portion thereof. Around the opening Q5 are disposed holes H1 to H4 for inserting the auxiliary shafts S1 to S4 (FIG. 1) and holes J1 to J4 for passing the main shafts L1 to L4 (FIG. 3) therethrough.

A tubular member 71 is fixed to the opening Q5 of the plate P5 via a collar 72. The front end of the tubular member 71 has a cut-out portion at an angle of 45 relative to the axis center thereof, and a dichroic mirror 73 is attached to the cut-out portion.

Figure 12:
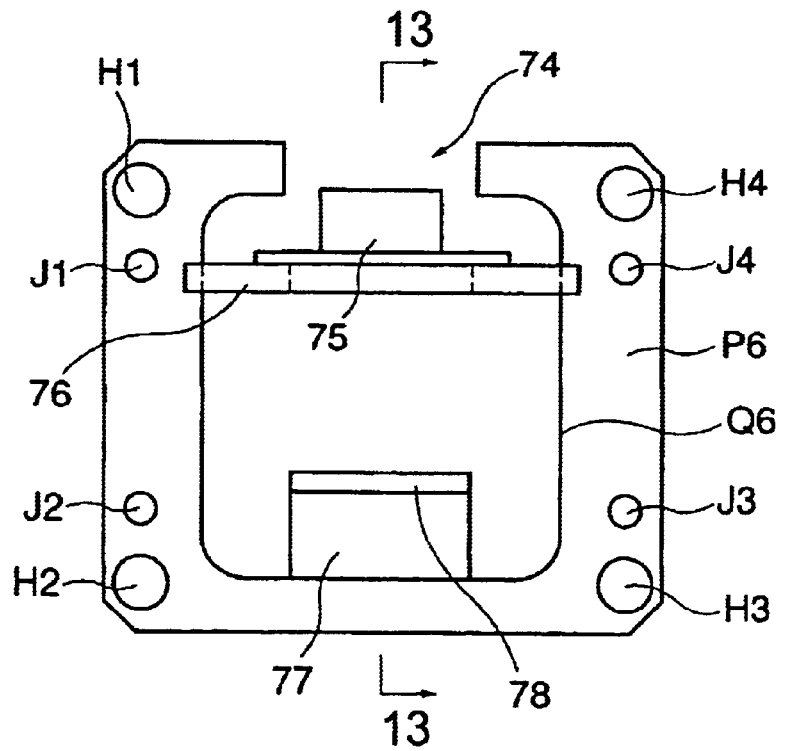
FIG. 12 is a front view showing a fifth optical element section according to the embodiment of the present invention.
Figure 13:
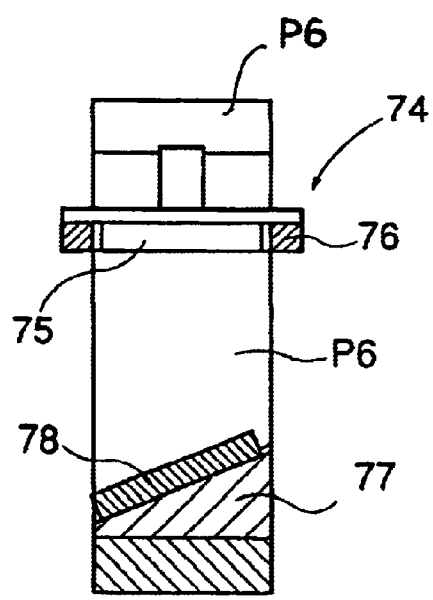
FIG. 13 is a cross-sectional view cut along the line E—E of FIG. 12.

Next, a fifth optical element section 74 is mounted onto the plate P6 as shown in FIGS. 12 and 13. The plate P6 is a rectangular flat plate such as shown in FIG. 12, and includes a square opening section Q6 whose upper portion reaches the outer peripheral surface of the plate P6. Around the opening section Q6 are disposed holes H1 to H4 for inserting the auxiliary shafts S1 to S4 (FIG. 1) and holes J1 to J4 for passing the main shafts L1 to L4 (FIG. 3) therethrough.

A ¼-inch-size CCD board camera 75 serving as an image capturing element is mounted on the holding plate 76, and the holding plate 76 is fixed to front and rear surfaces of the plate P6 by screws (not shown). A holding piece 77 is fixed onto a lower inner wall surface of the opening Q6, and a plane mirror 78 is mounted onto the holding piece 77.

Figure 14:
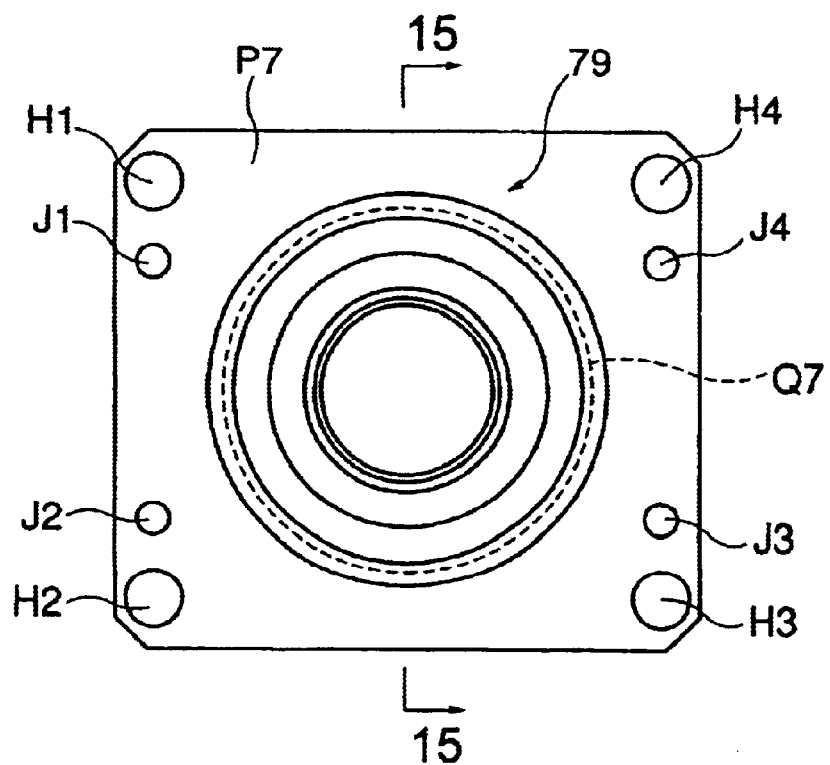
FIG. 14 is a front view showing a sixth optical element section according to the embodiment of the present invention.
Figure 15:
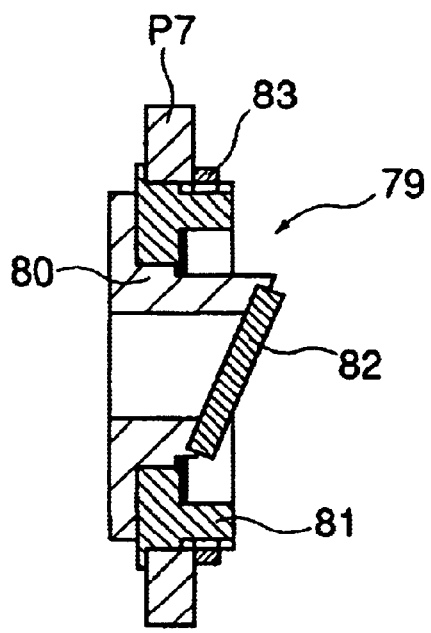
FIG. 15 is a cross-sectional view cut along the line F—F of FIG. 14.

Next, a sixth optical element section 79 is mounted on the plate P7 as shown in FIGS. 14 and 15. The plate P7 is a rectangular flat plate such as shown in FIG. 14, and includes a circular opening Q7 at a central portion thereof. Around the opening Q7 are disposed holes H1 to H4 for inserting the auxiliary shafts S1 to S4 (FIG. 1) and holes J1 to J4 for passing the main shafts L1 to L4 (FIG. 3) therethrough.

A tubular member 80 is fixed to the opening Q7 of the plate P7 via a collar 81. A front end of the tubular member 80 has a cut-out portion inclined relative to the axis center, and a plane mirror 82 is attached to the cut-out portion. The collar 81 is fixed to the plate P7 by engaging the nut 83 with an outer thread of the collar 81.

Here, at the time of processing the plates P1 to P7, seven aluminum plates having thicknesses corresponding to the plates P1 to P7 are superposed, and each side is cut simultaneously so that the aluminum plates may have an outer dimension of 58 mm×54 mm. Also, the superposed cut plates P1 to P7 are drilled simultaneously to form the holes H1 to H4 and the holes J1 to J4, so that the holes may be parallel to the side surfaces of the plates P1 to P7. Circular openings Q1, Q2, Q5, Q7 are formed at the center of the respective plates so that the inner wall surfaces of the circular openings Q1, Q2, Q5, Q7 may be parallel with the side surfaces of the plates. Similarly, the square openings Q3, Q6 are formed so that the inner wall surfaces of the square openings Q3, Q6 may be parallel with the side surfaces of the plates.

The plates P1 to P7 thus incorporating the respective optical element sections are assembled as shown in FIG. 2, by passing the main shafts L1 to L4 as shown in FIG. 3. This allows the plates P1 to P7 to be parallel with each other, and allows the optical axes of the optical elements to be parallel with the main shafts L1 to L4 and to coincide with each other. The optical path length can be adjusted by appropriately setting the spacing among the plates P1 to P7.

Figure 16:
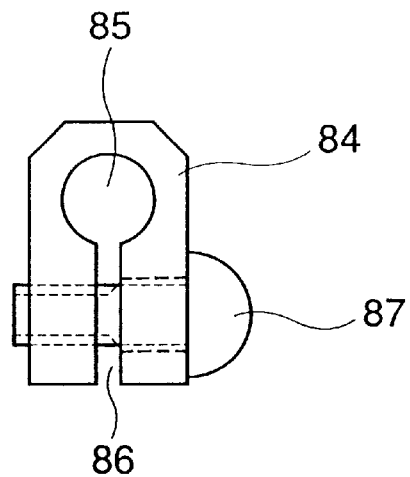
FIG. 16 is a front view showing a fixture to be used in the embodiment of the present invention.
Figure 17:
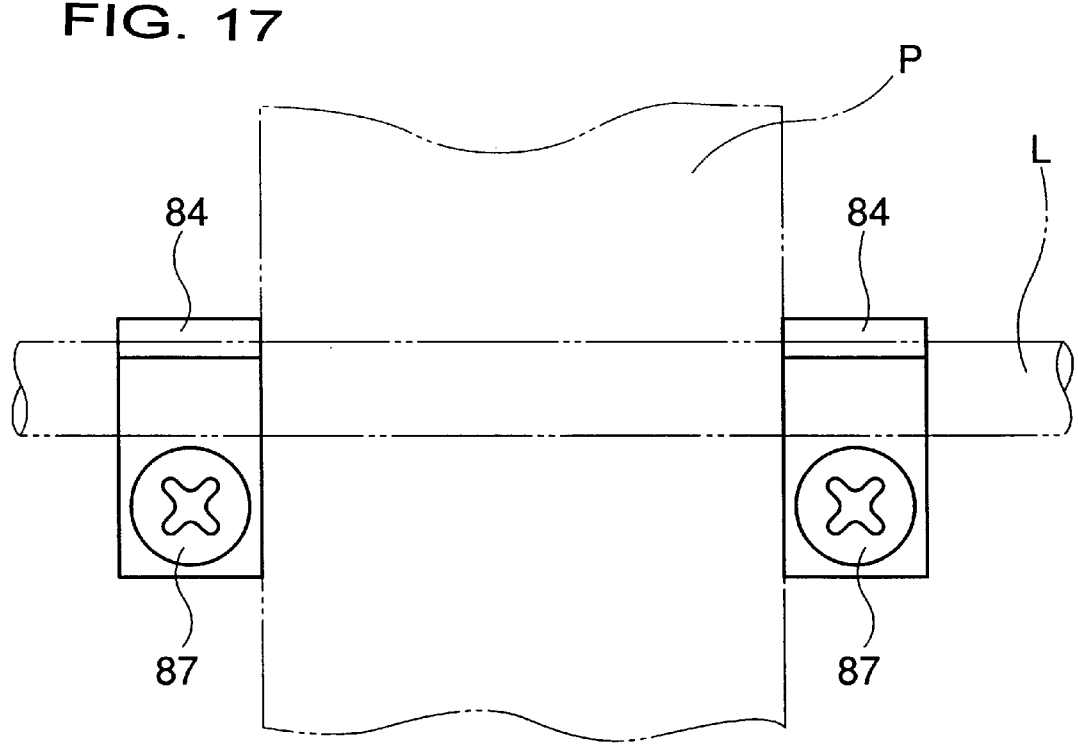
FIG. 17 is a side view showing a method of using the fixture to be used in the embodiment of the present invention.

Here, FIG. 16 shows a fixing piece for fixing the plates P1 to P7 to desired positions of the shafts L1 to L4. Referring to FIG. 16, the fixing piece 84 has a hole 85 corresponding to the cross-sectional shape and the size of the main shafts L1 to L4 and a split portion 86 and includes a screw 87 that engages with the screw hole that passes vertically through the split portion 86. Referring to FIG. 17, two fixing pieces 84 are inserted into the main shafts L to hold the plate P therebetween. The plate P is fixed to the shaft L by screwing the screw 87.

Here, the plurality of plates P7, P6, P5 may be fabricated as one block member, and the plates P4, P3 may be fabricated as one block member. The assembled frame section 24 is covered with side plates 88 to 90, as shown in FIG. 2.

Construction of a Second Unit (Light Source Section) 25

Figure 18:
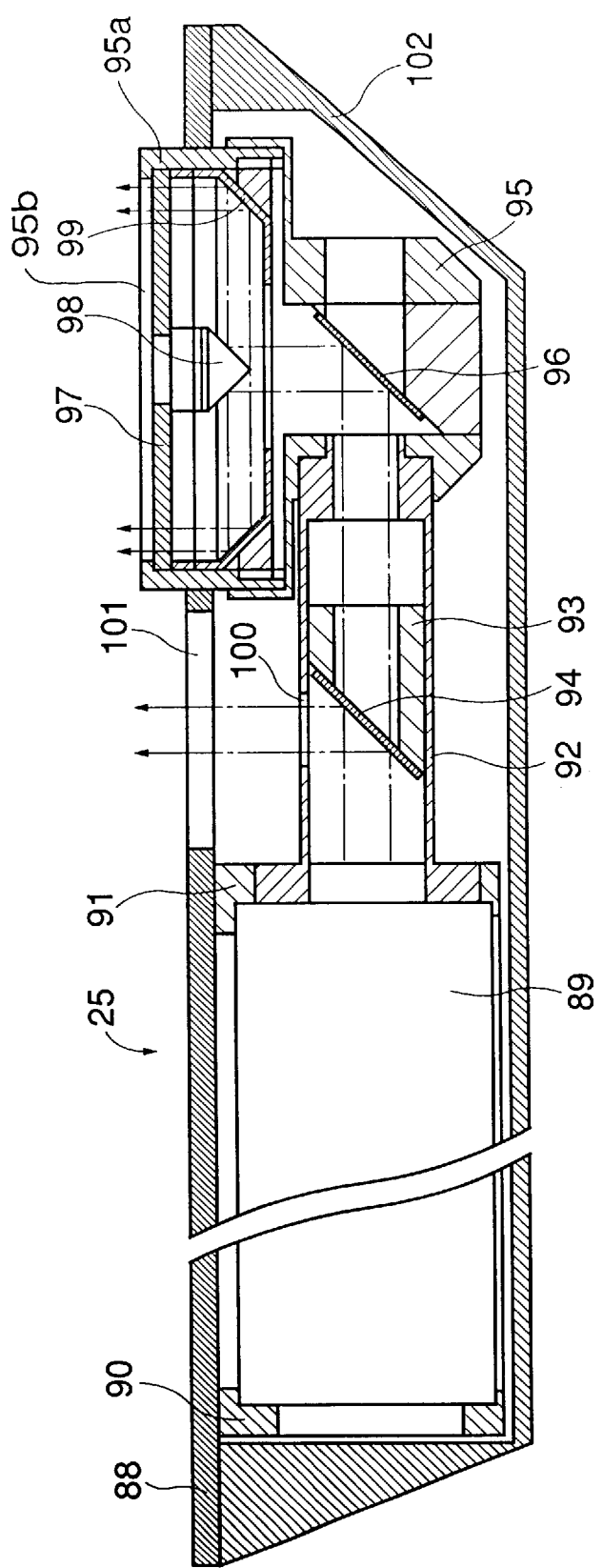
FIG. 18 is a cross-sectional view showing a light source section according to the embodiment of the present invention.

FIG. 18 is a cross-sectional view of a light source section 25, which includes windows 95b, 101 for supplying light beams to the first unit 24. A light beam having a first wavelength (635 nm) for dark-field illumination and a light beam having a second wavelength (880 nm) for dark-field illumination are emitted from the window 95b, and a light beam having a third wavelength (780 nm) for bright-field illumination is emitted from the window 101. A multiple light source unit 89 is mounted on the standard plate 88 by the holding members 90, 91 so that the optical axes may be parallel with the standard plate 88. A base end of the light guiding tube 92 is disposed at a light-emitting outlet of the multiple light source unit 89, and a dichroic mirror 94 is mounted in the inside of the light guiding tube 92 via a holding piece 93 at an angle of 45° relative to the optical axes. A terminal end of the light guiding tube 92 is connected to a holding piece 95.

The holding piece 95 holds a plane mirror 96 that reflects the light beam, which is emitted from the multiple light source unit 89, in a perpendicular direction. The holding piece 95 holds a conical external-reflection mirror 98 and holds a conical internal-reflection mirror 99 in the tubular member 95a via the glass disk 97.

The light-guiding tube 92 and the standard plate 88 include openings 100, 101, respectively, that passes the light beams reflected by the dichroic mirror 94.

The dichroic mirror 94 is a mirror that reflects the light beam having a wavelength of 780 nm and transmits the light beam having a wavelength of 635 nm and the light beam having a wavelength of 880 nm. Therefore, among the light flux emitted from the multiple light source unit 89, the light beam having a wavelength of 780 nm is reflected by the dichroic mirror 94 to be emitted perpendicularly to the standard plate 88. The light beam having a wavelength of 635 nm and the light beam having a wavelength of 880 nm are transmitted through the dichroic mirror 94 to be converted by the mirrors 96, 98, 99 into a light flux having an annular cross section that is emitted perpendicularly to the standard plate 88. The light source section 25 is covered with a housing 102.

The light source section 25 having such a construction is fixed onto the side plate 89 so that the tubular member 95a (FIG. 18) is inserted into the opening 89a (FIG. 2) of the side plate 89, thereby positioning the light source section 25. Further, the optical axis of the light beam from the multiple light source unit 89 is made parallel to the main shafts L1 to L4. Accordingly, as shown in FIG. 2, the light beam reflected by the dichroic mirror 94 impinges into a beam expander 56 with good precision, and the light flux having an annular cross section from the conical internal-reflection mirror 99 impinges onto the ring-shaped mirror 43 with good precision.

Figure 29:
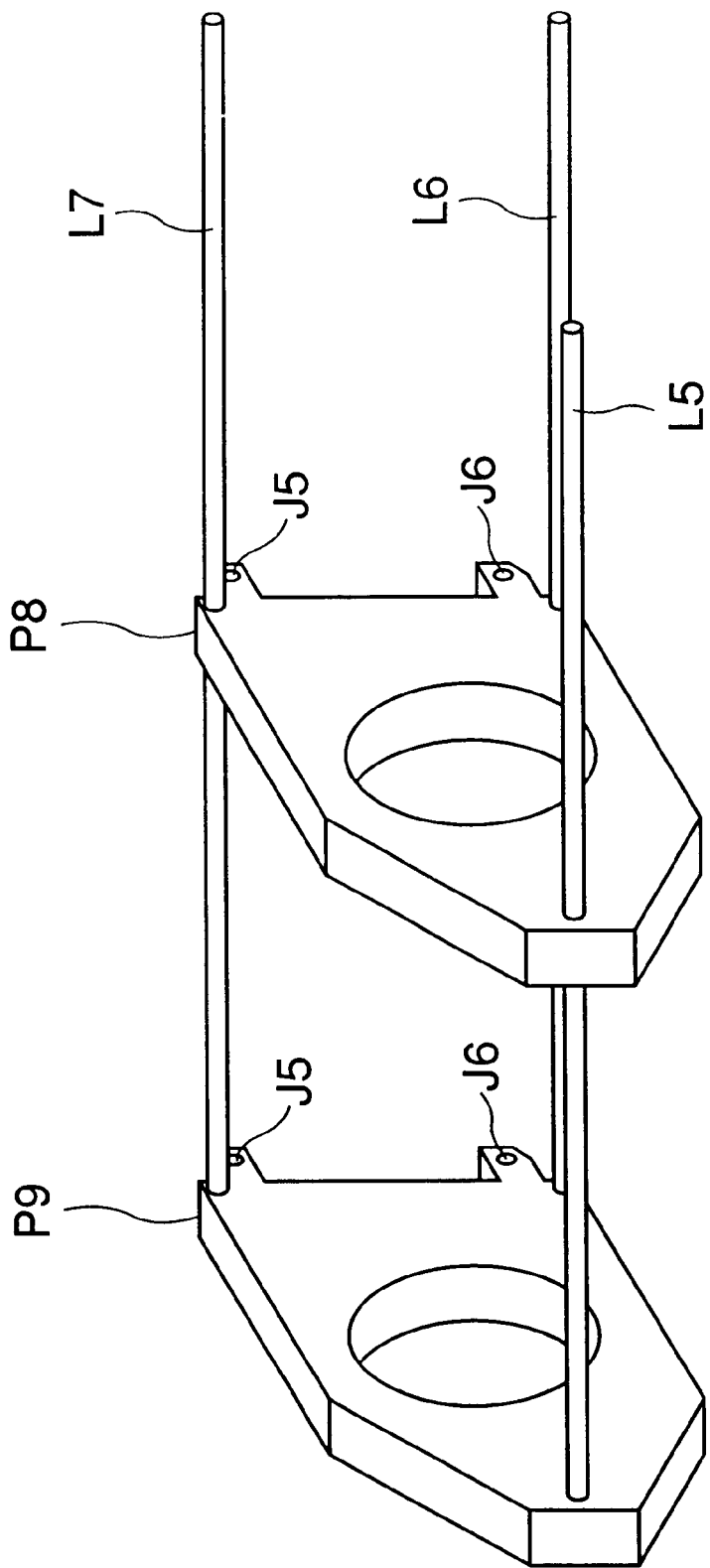
FIG. 29 is a perspective view showing a modified embodiment of the structure of the light source section shown in FIG. 18.

In the light source section 25 shown in FIG. 18, the multiple light source unit 89 is mounted by the holding members 90, 91 disposed on the standard plate 88. However, as shown in FIG. 29, the light source section 25 may be allowed to have a frame construction including parallel plates and shafts as in the case of the frame section 24. Namely, the holding members 90, 91 are made with plates P9, P8, respectively, and a plurality of shafts L5, L6, L7 are passed through the plates P9, P8 to fix the plates by means of the shafts. The plates P9, P8 include holes J5, J6 for passing the main shafts therethrough. The light source section 25 can be mounted to the frame section 24 by passing and fixing the main shafts L2, L3 of the frame section 24 through the holes J5, J6, respectively. The plate P9 is disposed between the plates P7 and P6, and the plate P8 is disposed between the plates P2 and P3.

Construction of Multiple Light Source Unit 89

Figure 19:
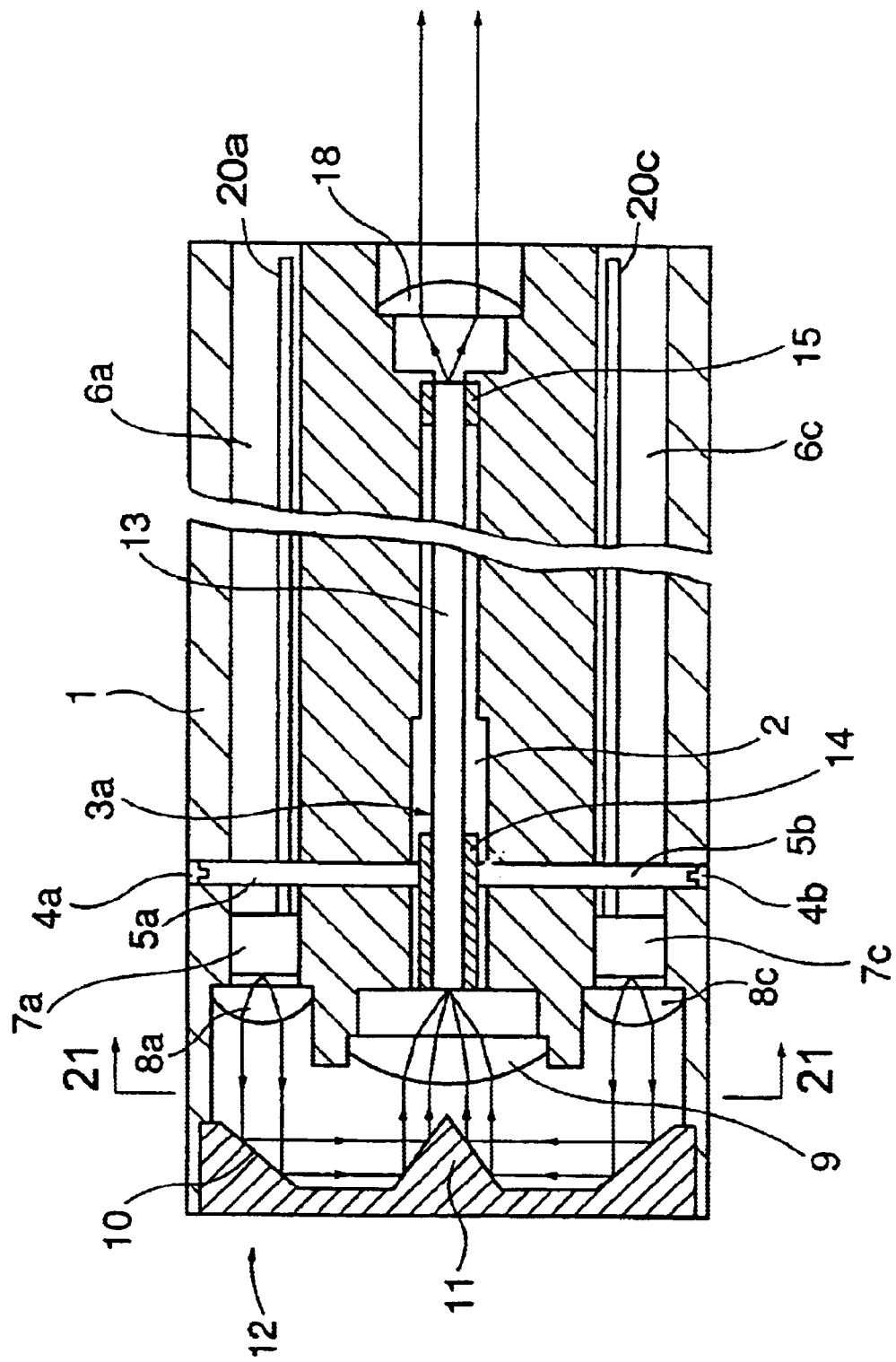
FIG. 19 is a cross-sectional view showing a multiple light source unit according to the embodiment of the present invention.
Figure 20:
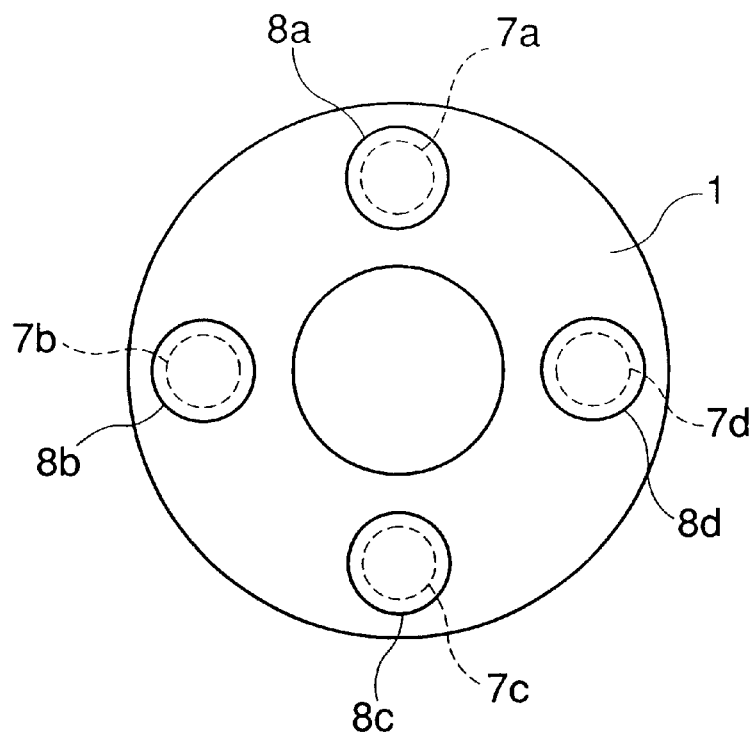
FIG. 20 is a front view showing an essential portion of the multiple light source unit according to the embodiment of the present invention.

FIG. 19 is a cross-sectional view showing a multiple light source unit 89, and FIG. 20 is a cross-sectional view cut along the line G—G of FIG. 19.

In these figures, a coherence reducing element 3a is inserted into a through-hole 2 disposed coaxially with a central axis of a cylindrical member 1. A front end of the coherence reducing element 3a is fixed by an inner wall of the through-hole 2, and a rear end of the coherence reducing element 3a is fixed by screws 5a, 5b respectively inserted in screw holes 4a, 4b formed perpendicularly to the central axis of the cylindrical member 1.

Further, the cylindrical member 1 includes four through-holes 6a, 6b, 6c, 6d (6b, 6d are not shown) that are parallel with the through-hole 2 and disposed on a circumference of a circle having a center located on the axis center of the cylindrical member 1. Light sources 7a, 7b, 7c, 7d and collimator lenses 8a, 8b, 8c, 8d are disposed at end portions of the through-holes 6a, 6b, 6c, 6d, respectively (See FIG. 20). Further, circuit boards 20a, 20b, 20c, 20d (20b, 20d are not shown) for driving the light sources 7a, 7b, 7c, 7d are disposed in the inside of the through-holes 6a, 6b, 6c, 6d, respectively.

Figure 21:
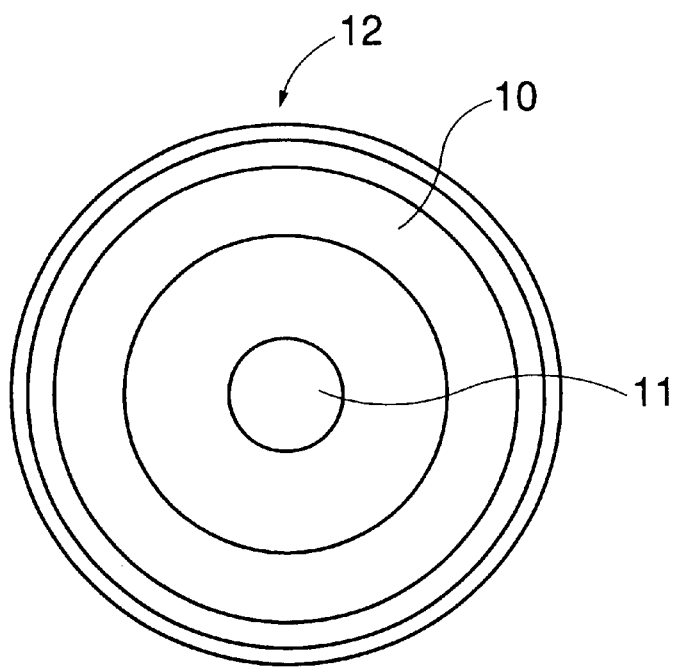
FIG. 21 is a cross-sectional view cut along the line G—G of FIG. 19.

A condensing lens 9 is disposed on the inlet side of the through-hole 2, and a collimator lens 18 is disposed on the outlet side of the through-hole 2. A mirror 12 including a conical internal-reflection mirror section 10 and a conical external-reflection mirror section 11 as shown in FIG. 21 is disposed on the left end surface of the cylindrical member 1 shown in FIG. 19. The mirror 12 is obtained by cutting an aluminum disk into a shape shown in FIGS. 19 and 21 and polishing its surface as a mirror, followed by vapor deposition of an Au film.

The coherence reducing element 3a is constructed with one multi-mode optical fiber 13 and protecting metal collars 14, 15 attached on both sides of the multi-mode optical fiber 13, as shown in FIG. 19. A large-diameter optical fiber (MKH-08 type manufactured by Sumitomo Electric Industries, Ltd.) is used as the multi-mode optical fiber 13.

A pulse semiconductor laser having a wavelength of 780 nm (L4356-02 type manufactured by Hamamatsu Photonics K.K.) is used as the light source 7a; pulse semiconductor lasers having a wavelength of 880 nm (L4356-02 type manufactured by Hamamatsu Photonics K.K.) is used as the light sources 7b, 7d; and a semiconductor laser having a wavelength of 635 nm is used as the light source 7c.

With this construction, the light beams emitted from the light sources 7a, 7b, 7c, 7d are converted into parallel light beams by the collimator lenses 8a, 8b, 8c, 8d to be reflected by the conical internal-reflection mirror section 10 of the mirror 12 in a direction perpendicular to the optical axis of the condensing lens 9 to be further reflected by the conical external-reflection mirror section 11 towards the condensing lens 9.

These light beams impinge into the condensing lens 9 in parallel and being spaced apart from each other at a predetermined distance from the optical axis of the condensing lens 9, to be further condensed by the condensing lens 9 to impinge into the light-receiving inlet of the coherence reducing element 3a at a predetermined equal angle of incidence. Here, since the optical path lengths from the light sources 7a, 7b, 7c, 7d to the condensing lens 9 are equal to each other, the light beams are incident into the light-receiving in let with the same spot diameter.

The coherence reducing element 3a mixes the incident light beams to reduce the coherence thereof and allows the light beams to exit from the light-emitting outlet towards the collimating lens 18 with flattened optical intensity distribution of the light beams. The collimating lens 18 converts the light beams from the coherence reducing element 3a into parallel light beams having a single optical axis.

Here, the condensing lens 9 is set in such a manner that the angle of incidence of the light beams incident into the light-receiving inlet of the coherence reducing element 3a is smaller than the maximum angle of incidence limited by the numerical aperture of the light-receiving inlet, thereby preventing the optical loss.

The positional relationship of the coherence reducing element 3a relative to the condensing lens 9 maybe adjusted by adjusting the screws 5a, 5b to allow the portion of the coherence reducing element 3a protected by the collar 14 to be shifted in a direction perpendicular to the central axis of the main body 1.

Figure 34:
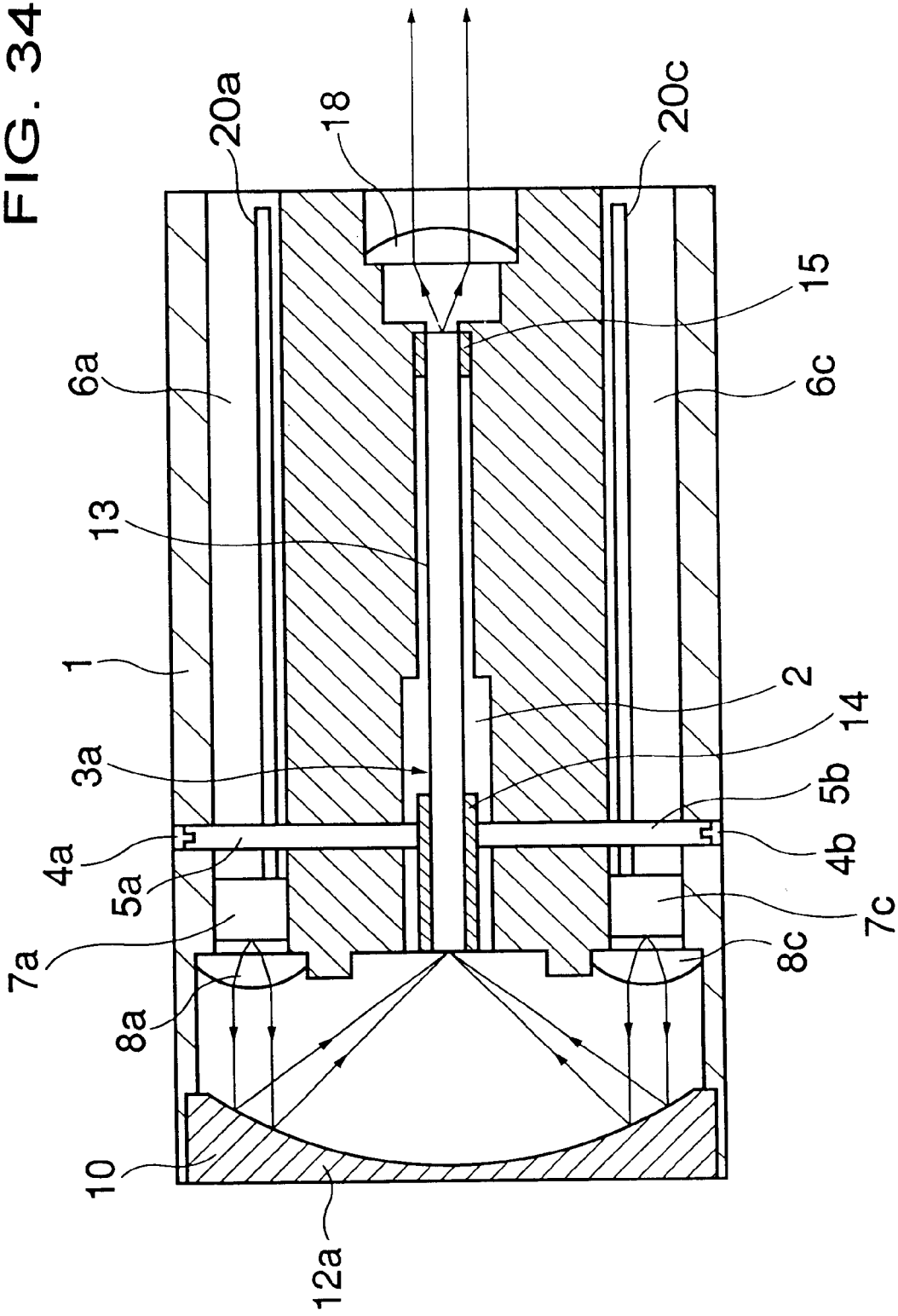
FIG. 34 is a cross-sectional view showing a modified embodiment of the multiple light source unit shown in FIG. 19.

FIG. 34 is a cross-sectional view showing another embodiment of a multiple light source unit. In this embodiment, the mirror 12 and the condensing lens 9 of the above embodiment (FIG. 19) are replaced with a concave mirror 12a, and the other constituent elements are the same as those of the embodiment shown in FIG. 19. Here, the coherence reducing element 3a is disposed in such a manner that its optical axis coincides with the optical axis of the concave mirror 12a and its light-receiving inlet is positioned at a focal point of the concave mirror 12a. The concave mirror 12a is fabricated by cutting an aluminum disk into a concave shape and polishing its surface as a mirror, followed by vapor deposition of an Au film.

With this construction, a plurality of light beams emitted from the light sources 7a, 7b, 7c, 7d are converted into light beams parallel to the optical axis of the concave mirror 12a by means of the collimator lenses 8a, 8b, 8c, 8d, and condensed by the concave mirror 12a to impinge into a light-receiving inlet of the coherence reducing element 3a at the same predetermined angle of incidence. Here, since the optical path lengths from the light sources 7a, 7b, 7c, 7d to the coherence reducing element 3a are equal to each other, all the light beams are incident into the light-receiving inlet, with the same spot diameters.

The coherence reducing element 3a mixes the plurality of incident light beams, reduces the coherence of these light beams, flattens the light intensity distribution, and emits the light beams through a light-emitting outlet to the collimator lens 18. The collimator lens 18 converts the light beams from the coherence reducing element 3a into a collimated light beam having a single optical axis.

Figure 30:
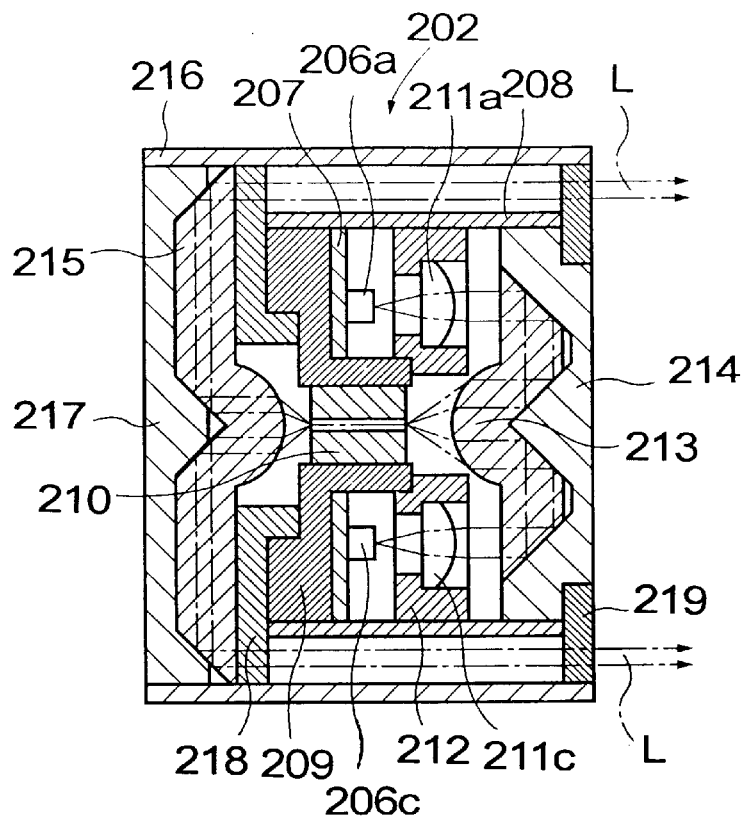
FIG. 30 is a cross-sectional view showing the modified embodiment of the light source section.

Alternatively, a system including a light source section 202 shown in FIG. 30 may be adopted in place of the light source section 25. Hereafter, the system will be explained. Here, it is to be noted that only a light flux having an annular cross section is created.

Figure 31:
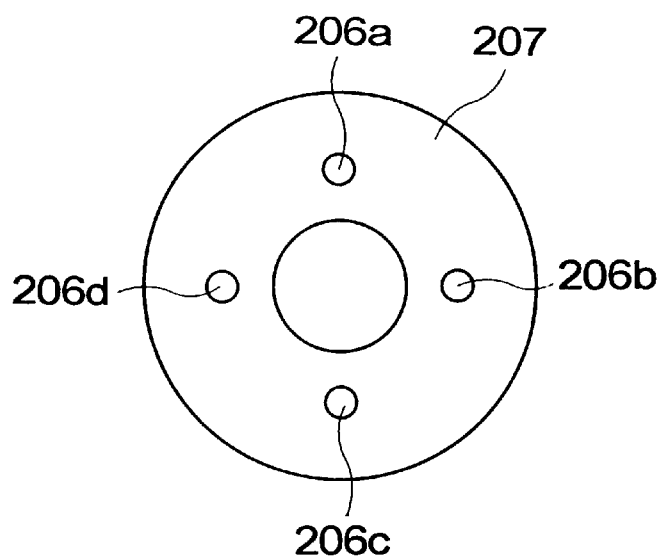
FIG. 31 is an explanatory view showing an arrangement of a light emitting element of the light source section shown in FIG. 30.

Referring to FIG. 30, four light emitting elements 206a to 206d are disposed with equal spacing on the same circumference on a substrate 207 located approximately at the center of the light source section 202, as shown in FIG. 31. The substrate 207 is supported by a supporting member 209 located inside the tubular member 208. The supporting member 209 includes an optical guiding element 210 at a central portion thereof. Collimator lenses 211a to 211d (211b and 211d are not shown) are supported by a supporting member 212 at a position opposite to the light-emitting elements 206a to 206d. The supporting member 212 is fixed to the supporting member 209.

Figure 32:
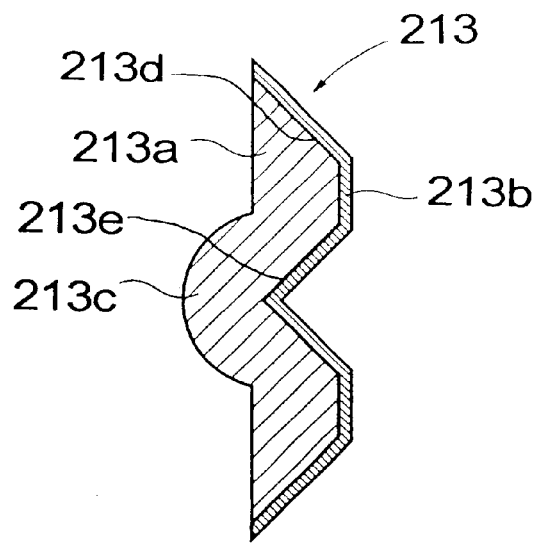
FIG. 32 is a cross-sectional view of a lens-mirror in the light source section shown in FIG. 30.

A lens-mirror 213 (a mirror with a lens) has a cross-sectional shape such as shown in FIG. 32. Namely, aluminum is deposited on one surface of a disk-like light-transmitting member 213a made of an acrylic resin to form a reflection film 213b as a reflection mirror, and the other surface is made into a concave shape at its center to form a lens 213c. The lens-mirror 213 is supported by a supporting member 214 fixed to an end portion of the tubular member 208. The lens-mirror 213 includes a first mirror (a conical internal-reflection mirror 213d and a conical external-reflection mirror 213e) and a condensing lens 213c.

Figure 33:
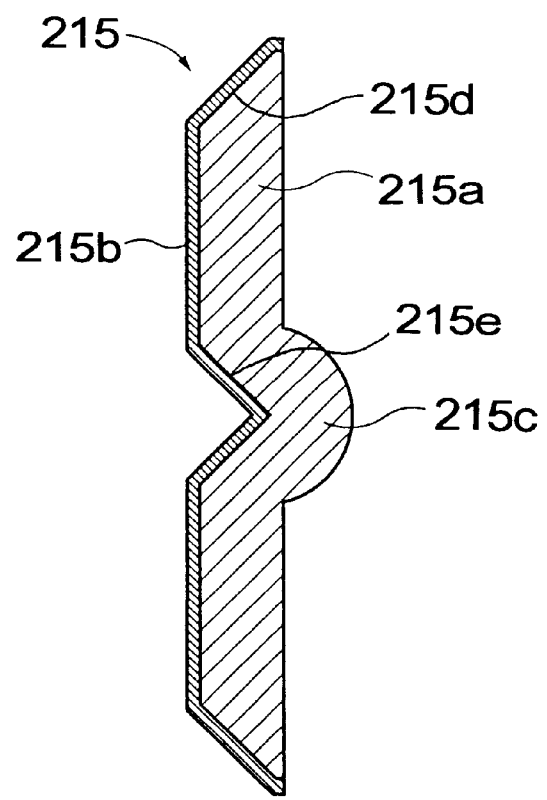
FIG. 33 is a cross-sectional view of another lens-mirror in the light source section shown in FIG. 30.

A lens-mirror 215 has a cross-sectional shape such as shown in FIG. 33. Namely, aluminum is deposited on one surface of a disk-like light-transmitting member 215a made of an acrylic resin to form a reflection film 215b, and the other surface is made into a convex shape at its center to form a lens 215c. The lens-mirror 215 is supported by a supporting member 217 fixed to an end portion of the tubular member 216. The lens-mirror 215 includes a second mirror (a conical internal-reflection mirror 215e and a conical external-reflection mirror 215d) and a collimator lens 215c.

Referring to FIG. 30, the supporting member 209 and the supporting member 214 are fixed to an inside wall of the tubular member 216 respectively via light-transmitting supporting members 218, 219 made of an acrylic resin. Here, pulse semiconductor lasers having a wavelength of 880 nm are used as the light-emitting elements 206a to 206c, and a red semiconductor laser having a wavelength of 635 nm is used as the light-emitting element 206d.

In the light source section 202 constructed as above, the light beams emitted from the light-emitting elements 206a to 206d are converted into parallel light beams by the collimator lenses 211a to 211d, respectively. The light beams thus converted into parallel light beams are reflected by the conical internal-reflection mirror 213d and the conical external-reflection mirror 213e of the lens-mirror 213 and condensed by the lens section 213c to be guided to the light-receiving inlet of the light-guiding element 210. The light-guiding element 210 mixes the light beams incident through the light-receiving inlet and allows the light beams to exit through the light-emitting outlet of the light guiding element 210 with reduced coherence.

The light beams emitted from the light guiding element 210 impinges into the lens section 215c of the lens-mirror 215 to be converted into parallel light beams, which are then reflected by the conical external-reflection mirror 215e and the conical internal-reflection mirror 215d to be converted into a light flux L having an annular cross section.

The light beams from the light emitting elements 206a to 206d are condensed into the light guiding element 210 and mixed. Therefore, the light source section 202 can emit the light flux L having an annular cross section if at least one of the light emitting elements is activated. Here, in this embodiment, an optical fiber (a kaleidoscope made by Sumitomo Electric Industries, Ltd.) is used as the light guiding element 210.

Construction of Third Unit (Light Receiving Section) 26

Figure 22:
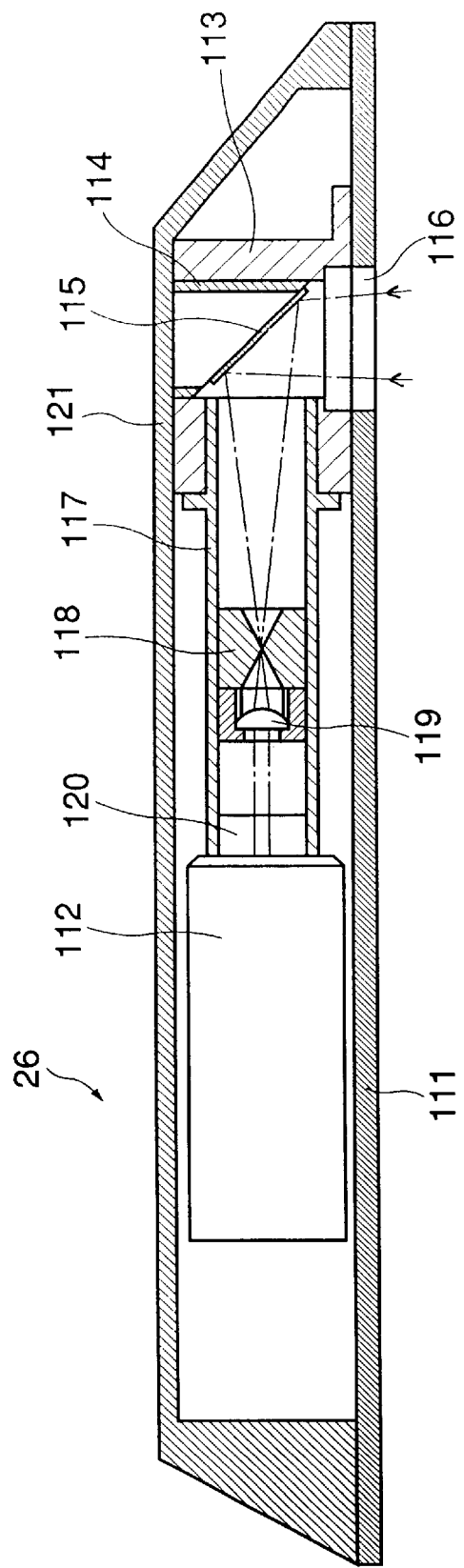
FIG. 22 is a cross-sectional view showing a light receiving section according to the embodiment of the present invention.

FIG. 22 is a cross-sectional view of a light-receiving section 26 including an optical detecting element. An optical detecting element (photomultiplier tube) 112 is disposed on a standard plate 111. A plane mirror 115 is disposed at an angle (obliquely) in a holding piece 113 via a tubular member 114, whereby the light beams incident through an opening 116 of the standard plate 111 are reflected perpendicularly towards the optical detecting element 112. A light guiding tube 117 connects the holding piece 113 with the optical detecting element 112, and includes a pinhole plate 118, a collimator lens 119, and a bandpass filter 120 in the inside.

In other words, the light beams incident through the opening 116 are received by the optical detecting element 112 via the mirror 115, the pinhole plate 118, the collimator lens 119, and the bandpass filter 120. Here, the light receiving section 26 is covered by a housing 121.

The light-receiving section 26 thus constructed is fixed onto a side plate 88 (FIG. 2) so that the tubular member 47 (FIG. 47) may be inserted into the opening 116 (FIG. 22), there by positioning the light-receiving section 26. Also, the optical axes of the optical elements constituting the light-receiving section 26 are made parallel to the main shafts L1 to L4. Therefore, the light beams transmitted through the condensing lens 46 impinge into the optical detecting element 112 with good precision.

Construction of Fifth Unit (Second Light Source Section) 23

Figure 23:
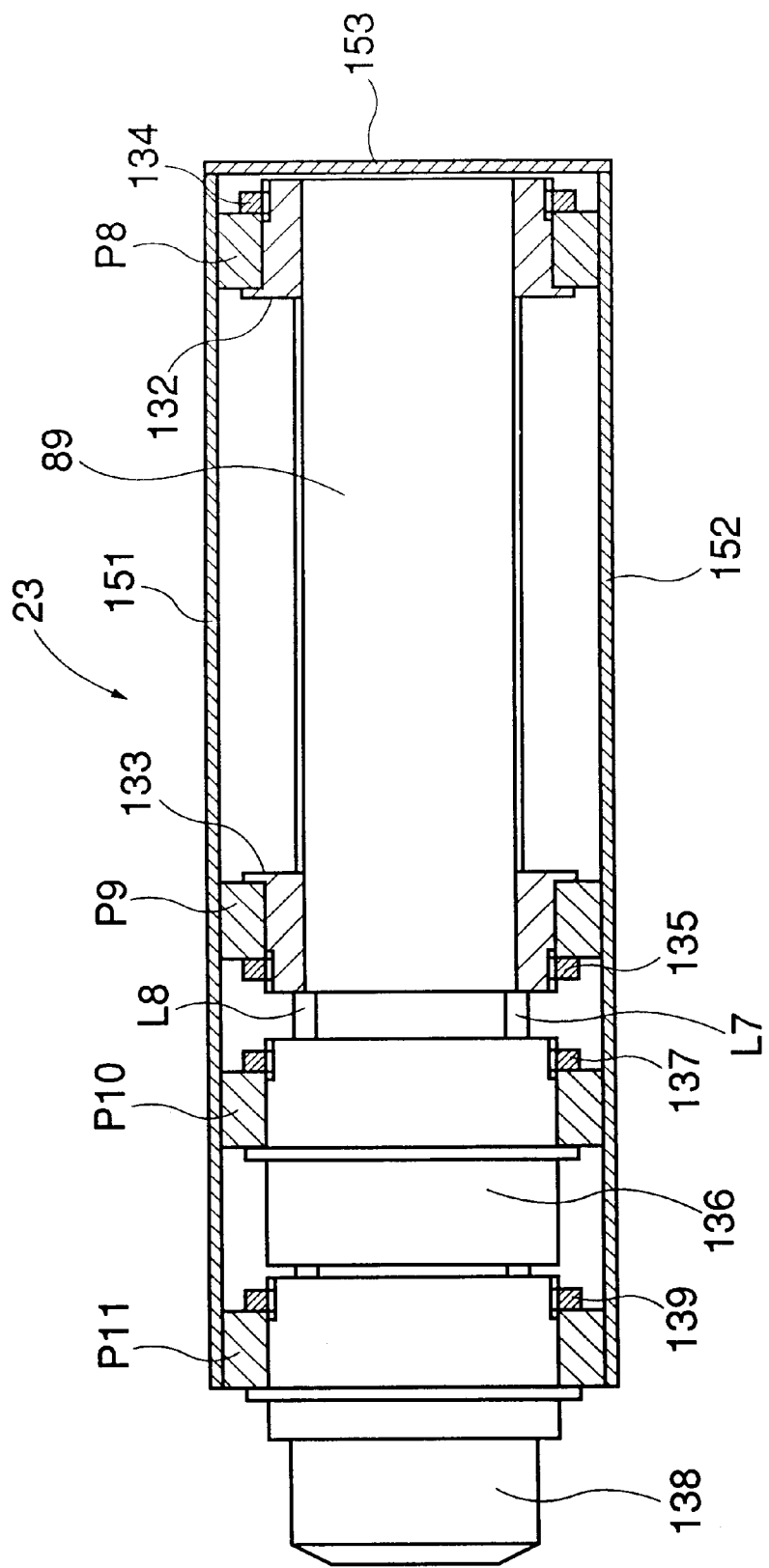
FIG. 23 is a cross-sectional view showing a second light source section according to the embodiment of the present invention.
Figure 24:
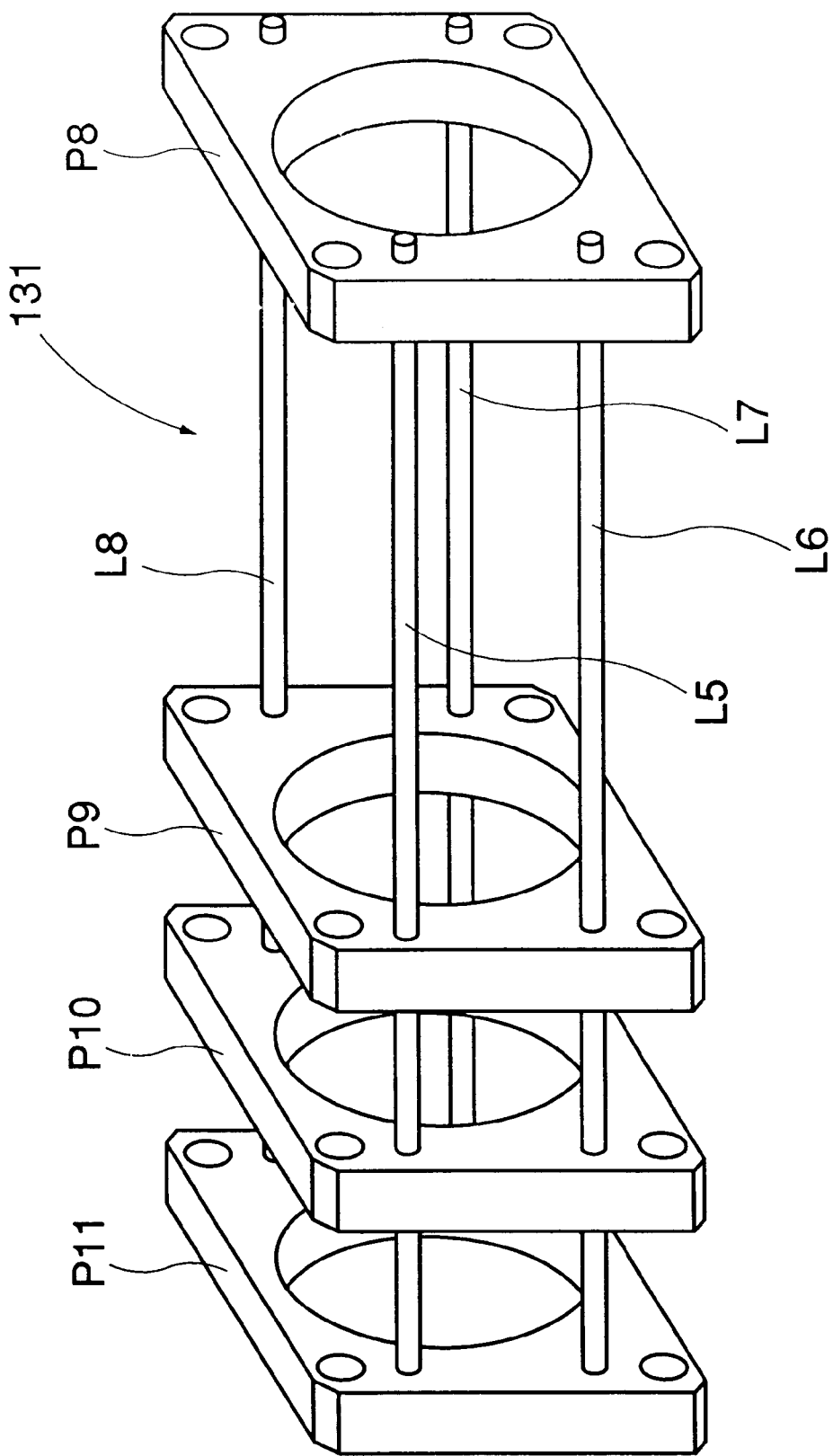
FIG. 24 is a perspective view showing a frame to be used for the second light source section according to the embodiment of the present invention.

FIG. 23 is a cross-sectional view of a second light source section (light source section for transmittance illumination). FIG. 24 is a perspective view of a frame 131 included in the light source section 23 for transmittance illumination. As shown in these figures, the frame 131 includes four plates P8 to P11 and four main shafts L5 to L8. The main shafts L5 to L8 pass vertically through the plates P8 to P11, and the plates P8 to P11 are arranged parallel to each other and spaced apart from each other at a predetermined distance to be fixed to the main shafts L5 to L8.

Necessary optical elements are respectively mounted on the plates P8 to P11 in the same manner as the plates P1 to P7 of the aforementioned frame section 24 before the plates P8 to P11 are fixed to the main shafts L5 to L8.

Figure 25:
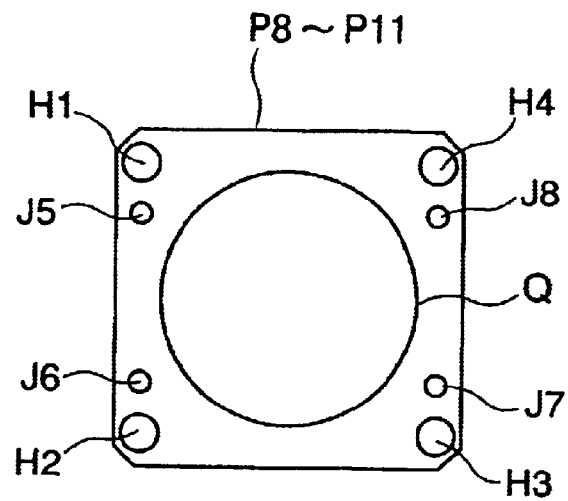
FIG. 25 is a front view showing a plate to be used for the frame shown in FIG. 24.

The plates P8 to P11 are rectangular flat plates as shown in FIG. 25, and include a circular opening Q at the center thereof. Around the opening Q are disposed holes H1 to H4 for inserting the auxiliary shafts S1 to S4 (FIG. 1), respectively, and holes J5 to J8 for passing the main shafts L5 to L8 (FIG. 24) therethrough, respectively. The plates P8 to P11 are processed in the same manner as the plates P1 to P7.

Referring to FIG. 23, a multiple light source unit 89 (See FIG. 19) is inserted into the openings Q of the plates P8 and P9 via collars 132, 133 with an external thread and fixed by engaging nuts 134, 135 with collars 132, 133.

A beam expander 136 is fixed to the plate P10 by means of a nut 137, and a condensing lens 138 is fixed to the plate P11 by means of a nut 139.

Referring to FIG. 23, the plates P8 to P11 thus incorporating the optical elements are assembled by passing the main shafts L5 to L8 therethrough, as shown in FIG. 24. This makes the plates P8 to P11 parallel to each other and positions the optical elements, thereby allowing the optical axes to coincide with each other.

The optical path length can be adjusted by appropriately setting the distances among the plates P8 to P11. The plates P8 to P11 are fixed to the main shafts L5 to L8 by means of the fixing piece 84 shown in FIG. 16. The light source 23 for transmittance illumination assembled as shown in FIG. 23 is covered with the side plates 151 to 153.

Construction of Fourth Unit (Placing Section) 22

Figure 26:
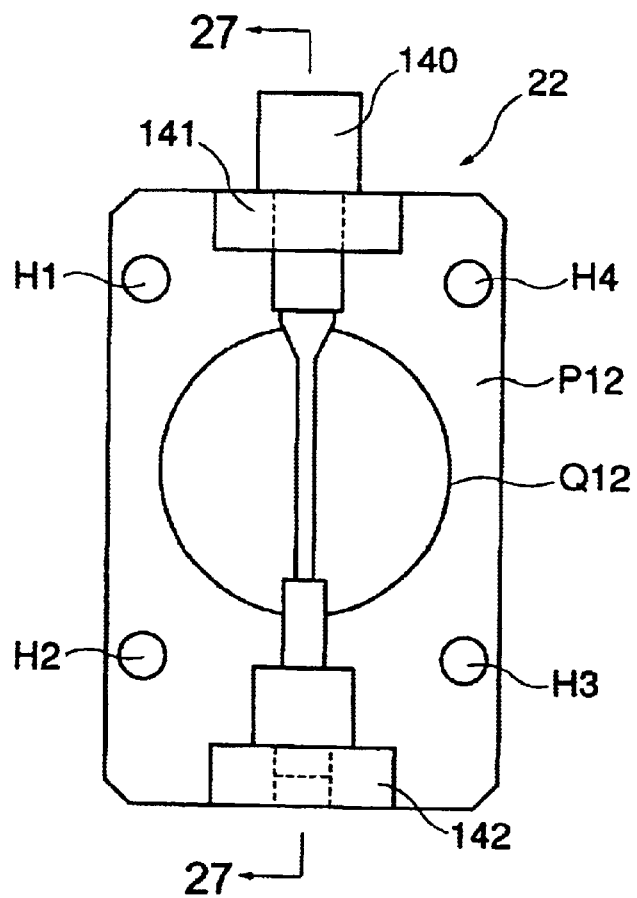
FIG. 26 is a front view showing a mounting section according to the embodiment of the present invention.
Figure 27:
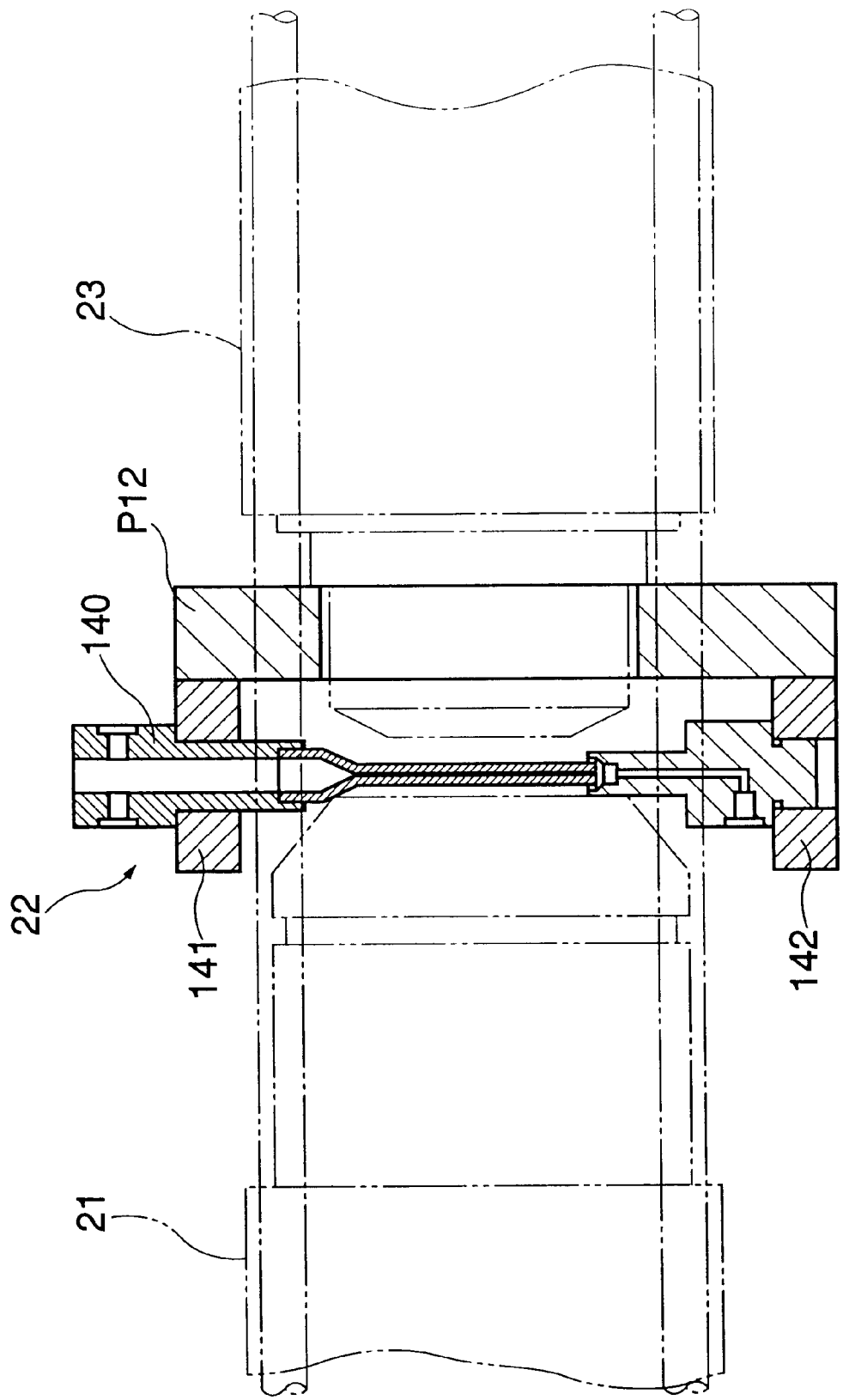
FIG. 27 is a cross-sectional view cut along the line H—H of FIG. 26.

FIG. 26 is a front view of a placing section 22, and FIG. 27 is a cross-sectional view cut along the H—H line of FIG. 26. The placing section 22 includes a plate P12. The plate P12 is a rectangular flat plate and includes a circular opening Q12 at its center and holes H1 to H4 for inserting the auxiliary shafts S1 to S4 (FIG. 1) therethrough, respectively.

In this Example, a sheath flow cell 140 is placed on the placing section 22 as an object and fixed to the plate P12 by supporting pieces 141, 142. For example, a sample liquid containing particles may be allowed to flow through the sheath flow cell 140 to detect a scattered light signal from the particles or to capture images of the particles. However, the object is not limited to the sheath flow cell alone.

Operation of Apparatus as a Whole

The main body 21, the placing section 22, and the second light source section 23 having the above-mentioned constructions are connected in series, as shown in FIGS. 1 and 27, by inserting the auxiliary shafts S1 to S4 through the holes H1 to H4 of the plates, respectively. At this time, the optical axis of the object lens 32 of the main body 21 coincides with the optical axis of the second light source section 23.

According to this apparatus, various optical information measurements such as follows can be made.

1. Measurement of Scattered Light Intensity by Dark Field Illumination

Figure 28:
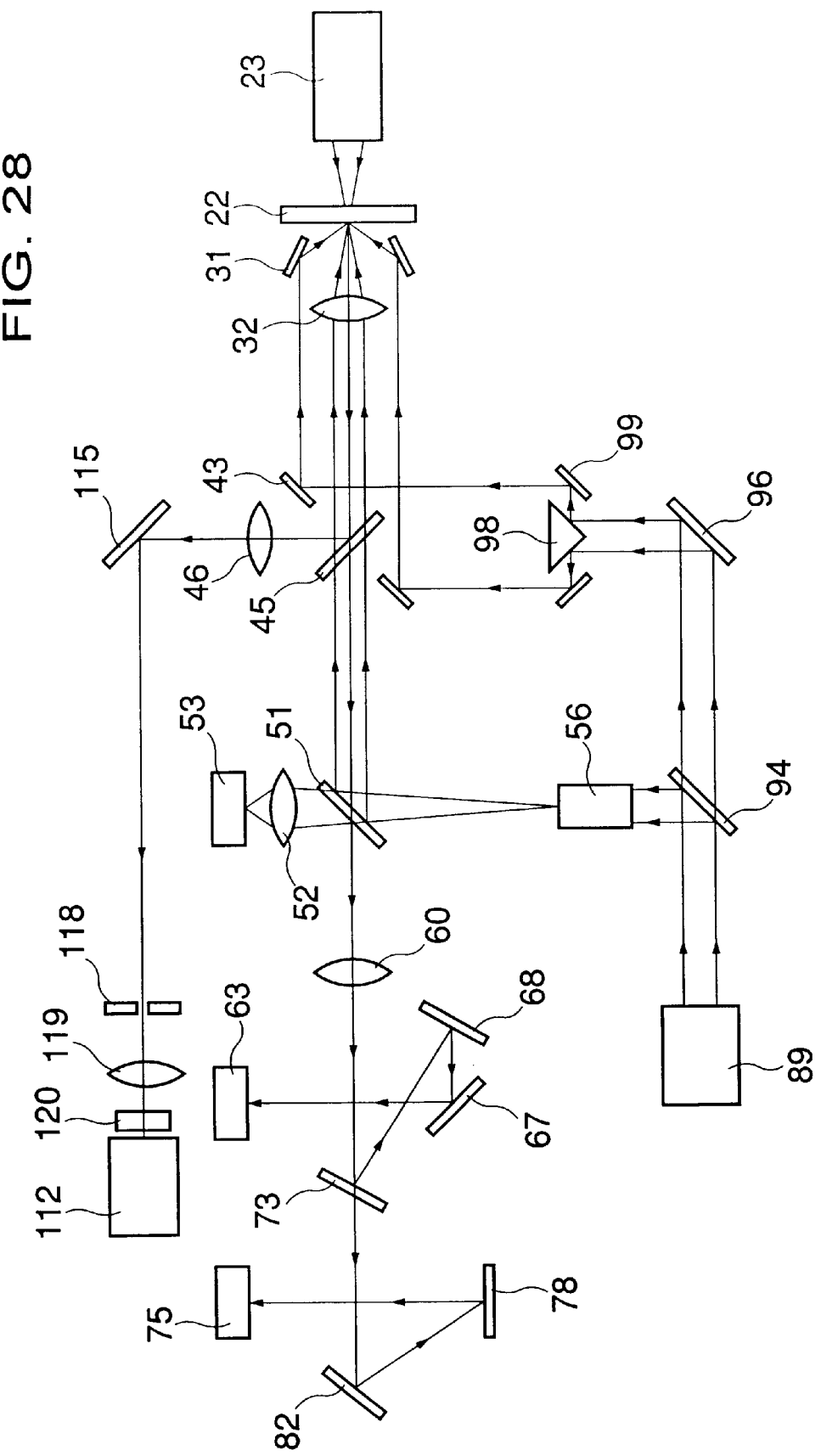
FIG. 28 is a view showing a configuration for explaining an operation of the embodiment of the present invention.

FIG. 28 is an explanatory view showing an overall construction of the apparatus. Referring to FIG. 28, when a laser light beam having a wavelength of 635 nm is emitted from the multiple light source unit 89, the laser light beam is transmitted through the dichroic mirror 94 and reflected by the mirror 96 to be converted into a light flux having an annular cross section by means of the conical external-reflection mirror 98 and the conical internal-reflection mirror 99. The light flux having an annular cross section is guided to the conical internal-reflection mirror 31 by the ring-shaped mirror 43 to converge on to the object placed on the placing section 22.

A scattered light beam (having a wavelength of 635 nm) from the illuminated object is reflected by the dichroic mirror 45 via the object lens 32 and impinge into the optical detecting element (photomultiplier tube) 112 via the mirror 115, the pinhole plate 118, the collimator lens 119, and the bandpass filter 120. This allows the optical detecting element 112 to measure an intensity of the scattered light beam from the object (for example, particle components in the sheath flow cell). Later-mentioned laser light beams may be emitted by pulse emission based on the signal detection of the optical detecting element 112.

2. Image Capturing by Dark Field Illumination

Referring to FIG. 28, when a pulse laser light beam having a wavelength of 880 nm is emitted from the multiple light source unit 89, the laser light beam is transmitted through the dichroic mirror 94 to perform dark field illumination of the object in the same manner as the aforementioned laser light beam having a wavelength of 635 nm.

An imaging light beam (having a wavelength of 880 nm) from the dark-field-illuminated object passes through the object lens 32 to be transmitted through the dichroic mirror 45 and further passes through the half mirror 51 and the imaging lens 60 to be transmitted through the dichroic mirror 73 to reach the CCD board camera 75 via the mirrors 82, 78. This allows the CCD board camera 75 to capture an image of the object by means of the pulse laser light beam having a wavelength of 880 nm.

3. Image Capturing by Bright-field Illumination

Referring to FIG. 28, when a pulse laser light beam having a wavelength of 780 nm is emitted from the multiple light source unit 89, the laser light beam is reflected by the dichroic mirror 94 and its beam diameter is enlarged by the beam expander 56. The, a half amount of the light beam is transmitted through the half mirror 51, and the remaining half amount of the light beam is reflected by the half mirror 51. The laser light beam reflected by the half mirror 51 is transmitted through the dichroic mirror 45 and converges onto the object by means of the lens 32. Namely, bright-field illumination is performed on the object.

An imaging light from the illuminated object passes through the object lens 32, the dichroic mirror 45, the half mirror 51, and the imaging lens 60 and is reflected by the dichroic mirror 73 to impinge into the CCD board camera 63 via the mirrors 67, 68. This allows the CCD board camera 63 to capture an image of the object by means of the bright-field illumination with the pulse laser light beam having a wavelength of 780 nm.

The laser light beam transmitted through the half mirror 51 impinges, via the lens 52, into the CCD board camera 53 for capturing images. This allows the CCD board camera 53 to detect an intensity of the pulse laser light beam having a wavelength of 780 nm emitted from the multiple light source unit 89 to correct an illumination blur of the images obtained by the CCD board camera 63.

4. Measurement of Transmitted Light Intensity by Transmittance Illumination

Referring to FIG. 28, when a laser light beam having a wavelength of 635 nm is emitted from the second light source 23, the laser light beam is transmitted through the object, and the transmitted light beam passes through the object lens 32 to be reflected by the dichroic mirror 45 and then passes through the mirror 115, the pinhole plate 118, the collimator lens 119, and the bandpass filter 120 to impinge into the optical detecting element 112. This allows the optical detecting element 112 to measure an intensity of the light beam transmitted through the object.

5. Image Capturing by Transmittance Illumination

Referring to FIG. 28, when a pulse laser light beam having a wavelength of 780 nm or 880 nm is emitted from the light source 23 for transmittance illumination, the light beam is transmitted through the object, and the obtained transmitted imaging light beam passes through the object lens 32, the dichroic mirror 45, the half mirror 51, and the imaging lens 60.

Then, if the laser light beam is an imaging light beam having a wavelength of 780 nm, the laser light beam is reflected by the dichroic mirror 73 and impinges into the CCD board camera 63 via the mirrors 67, 68. If the laser light beam is an imaging light beam having a wavelength of 880 nm, the laser light beam is transmitted through the dichroic mirror 73 and impinges into the CCD board camera 75 via the mirrors 82, 78. This allows images to be captured by transmittance illumination.

Since the optical information measuring apparatus of the present invention has a small size and excellent transportability as well as a good performance, it can be applied to the following uses.

(1) Observation of a state of cultured planktons.
(2) Measurement of particle components in an exhaust gas of an engine
(3) Measurement of particulate materials in an industrial plant
(4) Measurement of components in various beverages
(5) Inspection of wounds on a rail for train wheels
(6) Inspection of spun threads in the spinning industry
(7) Observation of surface wounds on a photosensitive plate in the photographing film industry
(8) Observation and image capturing of minute portions of highly integrated semiconductor IC chips
(9) Measurement of liquid drops of an atomized fuel for an engine
(10) Measurement of particles in a process of manufacturing powder bodies and particle bodies.

As shown and described above, according to the present invention, various optical elements are integrally mounted on a frame section, whereby the positioning of the optical elements is facilitated and a high arrangement density is provided. Therefore, a better performance is achieved and the size of the apparatus as a whole is reduced to provide an excellent transportability of the apparatus.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What we claim is:

1. An optical information measuring apparatus comprising:
   a light source element capable of emitting a light beam;
   light guiding optical elements for directing the light beam from the light source element to an object of measurement;
   a light receiving element for receiving the light beam from the object, the light receiving element including at least one optical detecting element for detecting the light beam from the object and an image capturing element for capturing an image of the object; and
   a frame including shaft members and block members which are supported at appropriate intervals by the shaft members, at least one of the block members supporting the light guiding optical elements, the block members including a first block member supporting the light source element and a second block member supporting the light receiving element.

2. The optical information measuring apparatus of claim 1, wherein the light guiding optical elements include an object lens.

3. The optical information measuring apparatus of claim 1, wherein the light guiding optical elements include a mirror.

4. The optical information measuring apparatus of claim 1, wherein each of the block members includes a plate having an opening at a central portion thereof.

5. The optical information measuring apparatus of claim 1, further comprising second light guiding optical elements for directing the light beam from the object to the light receiving element.

6. The optical information measuring apparatus of claim 5, wherein the second light guiding optical elements are partially used in common with the first light guiding optical elements.

7. The optical information measuring apparatus of claim 1, wherein each of the block members include respective bores therethrough for passing each of the shaft members.

8. The optical information measuring apparatus of claim 1, wherein the plurality of shaft members include three or more shaft members.

9. The optical information measuring apparatus of claim 1, further comprising an auxiliary frame unit connected to the frame and a placing part for placing the object, and wherein the placing part is mounted on the auxiliary frame unit.

10. The optical information measuring apparatus of claim 1, further comprising at least one other image capturing element for capturing an image of the object.

11. An optical information measuring apparatus comprising:
    a light source unit having the first and second light source elements;
    light guiding optical elements for directing light beams from the first and second light source elements to an object of measurement;
    a light receiving element for selectively receiving the light beams from the object, the light receiving element including at least one optical detecting element for detecting the light beam from the object and an image capturing element for capturing an image of the object; and
    a frame including connecting members and block members which are supported at appropriate intervals by the connecting members, at least one of the block members supporting the light guiding optical elements, the block members further including a first block member supporting the light source unit and a second block member supporting the light receiving element.

12. The optical information measuring apparatus of claim 11, wherein the light beam generated by the first light source element has a first wavelength and the light beam generated by the second light source element has a second wavelength different from the first wavelength.

13. The optical information measuring apparatus of claim 11, wherein the light guiding optical elements include an object lens.

14. The optical information measuring apparatus of claim 11, wherein the light source unit includes a light guiding element having an inlet part and an outlet part, the first and second light source elements being disposed around an optical axis of the light guiding element, and a light condensing element for condensing the light beams from the first and second light source elements to the inlet part of the light guiding element.

15. The optical information measuring apparatus of claim 14, further comprising a converting element for converting a light beam from the outlet part of the light guiding element into light flux having an annular cross section.

16. The optical information measuring apparatus of claim 11, wherein the light guiding optical elements include a mirror.

17. The optical information measuring apparatus of claim 11, wherein each of the block members includes a plate having an opening at a central portion thereof.

18. The optical information measuring apparatus of claim 11, further comprising second light guiding optical elements for directing the light beam from the object to the light receiving element.

19. The optical information measuring apparatus of claim 18, wherein the second light guiding optical elements are partially used in common with the first light guiding optical elements.

20. The optical information measuring apparatus of claim 13, further comprising an auxiliary frame unit connected to the frame and a placing part for placing the object, and wherein the placing part is mounted on the auxiliary frame unit.

21. The optical information measuring apparatus of claim 20, further comprising a second light source unit for supplying a light beam to the object, wherein the second light source unit is mounted on the auxiliary frame unit and aligned to the object lens with the placing unit disposed between the second light source unit and the object lens.

22. The optical information measuring apparatus of claim 11, further comprising another light receiving element for capturing the image of the object.

23. An optical information measuring apparatus comprising:
    a light source element capable of emitting a light beam;
    light guiding optical elements for directing the light beam from the light source element to an object of measurement;
    a light receiving element for receiving the light beam from the object; and
    a frame including shaft members and block members, the block members being supported at predetermined intervals by the shaft members, the block members supporting the light source element, the light guiding optical elements and the light receiving element.

24. An optical information measuring apparatus comprising:
- a light source unit having first and second light source elements;
- a light guiding unit including optical elements for directing light beams from the first and second light source elements to an object of measurement;
- a light receiving unit including elements for selectively receiving the light beams from the object; and
- a frame including connecting members and block members, the block members being supported at predetermined intervals by the connecting members, and the block members supporting the light source unit, the light guiding optical unit and the light receiving unit.

25. An optical information measuring apparatus comprising:
- a light source section including a light source for emitting a light beam of one or more wavelengths,
- a light guiding section including a plurality of optical elements for directing the light beams from the light source means to an object of measurement;
- a light receiving section including a plurality of elements for receiving the light beam reflected from the object of measurement, said light receiving section including at least one optical detecting element for detecting the light beam from the object and at least one image capturing element for capturing an image of the object; and,
- a frame section including a plurality of mutually parallel shaft members and a plurality of block members, said block members being supported at appropriate intervals by said shaft members, wherein a predetermined number of said block members support the elements of the light source section, a predetermined number of said block members supports the elements of the light guiding section, and a predetermined number of said block members supports the light receiving elements of the light receiving section, and
- wherein the light source section and the light receiving section are commonly mounted on the frame section and enclosed in a transportable housing enclosing said light source section, said light guiding section, said light receiving section, and said frame section.

26. An optical information measuring apparatus comprising:
- a first light source section including a light source for emitting a light beam of one or more wavelengths,
- a light guiding section including a plurality of optical elements for directing the light beams from the light source to an object of measurement;
- a light receiving section including a plurality of elements for receiving the light beam reflected from the object of measurement, said light receiving section including at least one optical detecting element for detecting the light beam from the object and at least one image capturing element for capturing an image of the object; and,
- a primary frame section including a plurality of mutually parallel shaft members and a plurality of block members, said block members being supported at appropriate intervals by said shaft members, wherein a predetermined number of said block members support the elements of the first light source section, a predetermined number of said block members supports the elements of the light guiding section, and a predetermined number of said block members supports the light receiving elements of the light receiving section, and
- wherein the first light source section and the light receiving section are commonly mounted on the primary frame section and enclosed in a first transportable housing enclosing said first light source section, said light guiding section, said light receiving section, and said frame section;
- a second light source section for emitting a second light beam of one or more wavelengths through the object of measurement to the object lens and said light receiving section;
- wherein said second light source section is detachably connected to said first transportable housing, and wherein said second light section is mounted on an auxiliary frame section located in a second transportable housing.

* * * * *